US008722094B2

(12) United States Patent
Yoshida et al.

(10) Patent No.: US 8,722,094 B2
(45) Date of Patent: May 13, 2014

(54) SOLID DISPERSION AND PHARMACEUTICAL COMPOSITION OF THE SAME, AND PRODUCTION PROCESSES THEREOF

(75) Inventors: Kazushi Yoshida, Kawasaki (JP); Norimichi Okubo, Kawasaki (JP); Junichi Sakata, Kawasaki (JP); Hashime Kanazawa, Kawasaki (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 365 days.

(21) Appl. No.: 12/922,029

(22) PCT Filed: Mar. 10, 2009

(86) PCT No.: PCT/JP2009/054517
§ 371 (c)(1),
(2), (4) Date: Sep. 10, 2010

(87) PCT Pub. No.: WO2009/113522
PCT Pub. Date: Sep. 17, 2009

(65) Prior Publication Data
US 2011/0020455 A1   Jan. 27, 2011

(30) Foreign Application Priority Data

Mar. 11, 2008  (JP) ................... 2008-061126
Feb. 12, 2009  (JP) ................... 2009-030376

(51) Int. Cl.
*A61K 9/14*   (2006.01)
(52) U.S. Cl.
USPC ........................................... 424/489
(58) Field of Classification Search
USPC ........................................... 424/489
See application file for complete search history.

(56) References Cited

U.S. PATENT DOCUMENTS

| 5,204,119 A | 4/1993 | Shiobara et al. | |
|---|---|---|---|
| 2003/0054037 A1 | 3/2003 | Babcock et al. | |
| 2004/0132772 A1 | 7/2004 | Awad et al. | |
| 2005/0207990 A1* | 9/2005 | Funke et al. | 424/46 |

FOREIGN PATENT DOCUMENTS

| CN | 101120922 | 2/2008 |
|---|---|---|
| EP | 0 330 532 | 8/1989 |
| EP | 0 472 969 | 3/1992 |
| EP | 0904781 | * 3/1999 |
| EP | 1 493 433 | 1/2005 |
| EP | 1 618 895 | 1/2006 |
| JP | 2-049720 | 2/1990 |
| JP | 4-108739 | 4/1992 |
| JP | 4-159222 | 6/1992 |
| JP | 2001-523221 | 11/2001 |
| JP | 2003-500439 | 1/2003 |
| JP | 2004-010575 | 1/2004 |
| JP | 2004-238348 | 8/2004 |
| JP | 2005-501820 | 1/2005 |
| JP | 2005-047893 | 2/2005 |
| JP | 2006-506388 | 2/2006 |
| JP | 2006-512361 | 4/2006 |
| JP | 2006-248922 | 9/2006 |
| JP | 2007-508248 | 4/2007 |
| JP | 2007-508249 | 4/2007 |
| JP | 2007-161588 | 6/2007 |
| JP | 2008-133258 | 6/2008 |
| WO | 98/08490 | 3/1998 |
| WO | 98/31361 | 7/1998 |
| WO | 00/72829 | 12/2000 |
| WO | 03/000238 | 1/2003 |
| WO | 2004/039349 | 5/2004 |
| WO | 2004/056395 | 7/2004 |
| WO | 2004/096280 | 11/2004 |
| WO | 2005/034908 | 4/2005 |
| WO | 2005/034920 | 4/2005 |
| WO | 2005/087199 | 9/2005 |
| WO | 2008/104852 | 9/2008 |

OTHER PUBLICATIONS

Asahi (Asahi Glass Sunsphere data sheet; http://www.agc.com/english/chemicals/shinsei/gel/sun-gel.htm, viewed on Nov. 14, 2012).*
Miura et al. 2 (Chem. Pharm. Bull. 59(6) 686-691 (2011)).*
Sylysia (Fuji Sylysia data sheet; http://www.tcrindustries.com/Principals/BROCHURES/fujibrochures/FCP%20Brochurespdf, downloaded Nov. 14, 2012).*
Sylysia 2 (Fuji Sylysia data sheet 2; http://www.aquachem.co.kr/product/Sylysia.htm, viewed on Nov. 14, 2012).*
Machine translation of Miura et al. (machine translation of WO 2004096280).*
Farnier et al. (Am J Cardiol 2000;85:53-57).*
Sylysia (http://www.fuji-silysia.co.jp/english/product/micronized_silica/sylysia.html, 2003).*

(Continued)

*Primary Examiner* — David J Blanchard
*Assistant Examiner* — Devang Thakor
(74) *Attorney, Agent, or Firm* — Wenderoth, Lind & Ponack, L.L.P.

(57) ABSTRACT

A powdery porous carrier comprising a porous silicon-containing carrier is impregnated with a solution containing an organic solvent and an active ingredient hardly soluble in water, and the organic solvent is removed to give a solid dispersion having the active ingredient supported to the porous carrier without a treatment with a supercritical fluid. The porous silicon-containing carrier has a heating loss of not more than 4% by weight at a temperature of 950° C. for 2 hours (e.g., a spherical silicon-containing carrier such as a spherical porous silica). The porous silicon-containing carrier may be a spherical silica having a mean pore size of 10 to 40 nm and an oil absorption of 175 to 500 ml/100 g. A pharmaceutical composition (e.g., tablets, granules, or capsules) may be prepared from the solid dispersion and a pharmaceutically acceptable carrier. This invention provides a solid dispersion and a pharmaceutical composition (or a pharmaceutical preparation) which allows improvement in a solubility and a bioavailability of an active ingredient hardly soluble in water (e.g., a fibrate compound).

26 Claims, 8 Drawing Sheets

(56) References Cited

OTHER PUBLICATIONS

Suciu (Journal of Colloid and Interface Science 259 (2003) 62-80).*
International Search Report issued May 26, 2009 in International (PCT) Application No. PCT/JP2009/054517.
H. Takeuchi et al., "Spherical Solid Dispersion Containing Amorphous Tolbutamide Embedded in Enteric Coating Polymers or Colloidal Silica Prepared by Spray-Drying Technique", Chemical & Pharmaceutical Bulletin, vol. 35, No. 9, pp. 3800-3806, 1987.
"Proceedings of the Annual Meeting of the Pharmaceutical Society of Japan", 121, 1999, p. 103 and partial English translation.
English translation of the International Preliminary Report on Patentability and Written Opinion dated Nov. 2, 2010.
Office Action issued Apr. 28, 2013 in corresponding Chinese Application No. 200980112995.8, with English translation.
Supplementary European Search Report issued Apr. 2, 2013 in corresponding European Application No. EP 09 71 8988.
Sanganwar et al., "Dissolution-rate enhancement of fenofibrate by adsorption onto silica using supercritical carbon dioxide", International Journal of Pharmaceutics, vol. 360, 2008, pp. 213-218.

* cited by examiner

SOLID DISPERSION AND PHARMACEUTICAL COMPOSITION OF THE SAME, AND PRODUCTION PROCESSES THEREOF This application is a U.S. national stage of International Application No. PCT/JP2009/054517 filed Mar. 10, 2009.

TECHNICAL FIELD

The present invention relates to a solid dispersion containing a powdery porous carrier and having an improved solubility (or dissolution rate) of an active ingredient (e.g., a fibrate-series active ingredient) hardly soluble in water, a pharmaceutical composition containing the solid dispersion, a process for producing the solid dispersion, and a process for producing the pharmaceutical composition.

BACKGROUND ART

An active ingredient hardly (or sparingly) soluble in water (e.g., a fibrate-series active ingredient) remarkably deteriorates bioavailability due to a low solubility (or dissolution rate) or dispersibility thereof. In order to improve the solubility of the active ingredient, various formulations have been examined, for example, pulverization of the active ingredient, a solid dispersion containing a carrier solubilizing an active ingredient and the active ingredient dispersed in the carrier, and a solid dispersion containing the active ingredient supported on or to a powdery porous carrier by impregnation.

For example, European Patent Application Publication No. EP330532 (Patent Document 1) discloses that the bioavailability of fenofibrate is improved by co-pulverizing a surfactant (particularly sodium lauryl sulfate) and fenofibrate. International Publication No. WO98/31361 pamphlet (Patent Document 2) discloses adding a hydrophilic polymer containing finely powdered fenofibrate and a surfactant, each suspended therein, to an inactive carrier for improving the bioavailability of fenofibrate. However, these preparations still have insufficient drug solubility (or dissolution rate) or dispersibility and unsatisfactory bioavailability. Moreover, the handleability in the production process is deteriorated with making the particle size of the active ingredient fine.

Japanese Patent Application laid-Open No. 2003-500439 (JP-2003-500439A, Patent Document 3) discloses a composition which is a eutectic mixture of a lipid-regulating agent such as a fibrate and a statin and an excipient such as a polyethylene glycol. Japanese Patent Application laid-Open No. 2007-161588 (JP-2007-161588A, Patent Document 4) discloses a solid dispersion prepared by melt-mixing fenofibrate and a polyethylene glycol and solidifying the mixture, and the proportion of the fenofibrate relative to the solid dispersion is not less than 50% by mass. However, in these solid dispersions, the species of a usable and meltable carrier component is strictly limited depending on the species of the pharmacologically active ingredient. Further, since the pharmacologically active ingredient and the carrier component are melt-mixed, these techniques can apply only to thermally stable ones.

Regarding a solid dispersion utilizing a porous carrier, for example, Chemical & Pharmaceutical Bulletin (Japan), 35(9), 1987, p. 3800-3806 (Non-Patent Document 1) discloses that the solubility of a hardly soluble drug is improved by using a colloidal silica, which is one of porous powders, as a carrier and spray-drying the drug in a water system. Proceedings of the Annual Meeting of the Pharmaceutical Society of Japan, 121, 1999, p. 103 (Non-Patent Document 2) discloses that a colloidal silica carrier is added to indomethacin or tolbutamide to change the crystallinity of the principal ingredient, thereby improving the solubility. In Japanese Patent Application laid-Open No. 2004-10575 (JP-2004-10575A, Patent Document 5), the solubility of itraconazole is improved by mixing an inorganic porous substance (such as calcium silicate or light anhydrous silic acid) to itraconazole. In Japanese Patent Application laid-Open No. 2004-238348 (JP-2004-238348A, Patent Document 6), the bioavailability of itraconazole is improved by adsorbing an itraconazole solution to or on a core material comprising silic acid or a salt thereof and/or coating a core material comprising silic acid or a salt thereof with an itraconazole solution. Japanese Patent Application laid-Open No. 2006-506388 (JP-2006-506388A, Patent Document 7) discloses a pharmaceutical composition and cosmetic composition containing a hydrophobic and highly dispersible silicon dioxide having a tamping density of 70 to 400 g/L. This document also refers to a BET specific surface area of silicon dioxide of 50 to 400 m$^2$/g. Japanese Patent Application laid-Open No. 2006-248922 (JP-2006-248922A, Patent Document 8) discloses a tablet obtained by compressing a mixture of a composite particle and other components, the composite particle being obtained by spray-drying a silica and a drug such as indomethacin or acetaminophen.

However, due to the bulkiness of a porous carrier such as silic anhydride, a size of a solid preparation is still large even if the solid dispersion is compressed. In particular, since the compression molding causes a strong bonding of the porous carrier such as silic anhydride, the dispersibility or disintegratability of the solid preparation is deteriorated, and therefore, the solubility (or dissolution rate) of the active ingredient is rather reduced.

International Publication No. WO 2004/096280 pamphlet (Patent Document 9) discloses a drug-containing composition obtainable by treating a composition containing a drug very hardly soluble in water and a porous substance with a supercritical liquid or subcritical liquid of carbon dioxide. This document exemplifies "SYLYSIA" (manufactured by Fuji Silysia Chemical Ltd.) and a fine-spherical porous silica "SUNSPHERE H-51" (manufactured by Asahi Glass Co., Ltd.) as silic acid or a salt thereof. The document mentions that the dissolution rate of the drug from the composition is improved. However, in order to improve the dissolution rate of the drug, it is essential to charge the drug and the porous substance in a pressure tight container, fill the container with carbon dioxide, and hot-pressurize the container for treating the drug and the porous substance with a supercritical liquid or subcritical liquid of carbon dioxide. Therefore, the process is industrially disadvantageous due to the complicated production steps. Further, when the composition is compressed for molding, the dispersibility or disintegratability of the resulting preparation is deteriorated, and the dissolution rate of the drug is reduced in some cases.

International Publication No. WO 2005/034920 pamphlet (Patent Document 10) discloses a solid oral dosage form comprising a fibrate dissolved in a hydrophobic, hydrophilic or water-miscible vehicle (a vehicle such as a polyethylene glycol) and a solid dosage form further comprising an excipient, and refers to Aeroperl (trademark) 300 (Degussa) as a carrier or excipient (oil-sorption material). This document discloses a method of manufacturing the solid oral dosage form comprising the steps of: bringing the vehicle in liquid form, maintaining the liquid vehicle at a temperature below the melting point of the fibrate, dissolving the desired amount of fibrate in the vehicle, spraying the resulting solution onto a solid carrier having a temperature below the melting point of the vehicle, mechanically working the resulting composition to obtain particles, and subjecting the particulate material to conventional methods for preparing solid dosage forms. However, this method requires to prepare a solid dispersion by heating and dissolving the fibrate in the vehicle and to spray the molten solid dispersion on the carrier. In the spraying step, a special spray apparatus is needed, and the operation is complicated. Moreover, a relatively large amount of the vehicle, compared with the fibrate, is required for preparing the solid dispersion. In addition, since the molten solid dispersion is sprayed for deposit on a solid carrier having a temperature below the melting point of the vehicle, the active ingredient is localized on the surface of the carrier and the solubility (or dissolution rate) of the fibrate from the solid dosage form depends on the molten solid dispersion containing the fibrate and the vehicle, whereby the solubility (or dissolution rate) of the fibrate cannot be improved greatly. Therefore, it is difficult to make a preparation compact or small as well as improve the bioavailability of the fibrate drastically even in a low fibrate content of the preparation.

[Patent Document 1] EP330532 (Claims)
[Patent Document 2] International Publication No. WO98/31361 pamphlet (Claims)
[Patent Document 3] JP-2003-500439A (Claims)
[Patent Document 4] JP-2007-161588A (Claims)
[Patent Document 5] JP-2004-10575A (Claims)
[Patent Document 6] JP-2004-238348A (Claims)
[Patent Document 7] JP-2006-506388A (Claims)
[Patent Document 8] JP-2006-248922A (Claims)
[Patent Document 9] International Publication No. WO 2004/096280 pamphlet (Claims)
[Patent Document 10] International Publication No. WO 2005/034920 pamphlet (Claims)
[Non-Patent Document 1] "Chemical & Pharmaceutical Bulletin" (Japan), 35(9), 1987, p. 3800-3806
[Non-Patent Document 2] "Proceedings of the Annual Meeting of the Pharmaceutical Society of Japan", 121, 1999, p. 103

DISCLOSURE OF THE INVENTION

Problems to be Solved by the Invention

It is therefore an object of the present invention to provide a solid dispersion having a remarkably improved solubility (or dissolution rate) or dispersibility and bioavailability of an active ingredient hardly soluble in water (e.g., a fibrate compound) in spite of the fact that the active ingredient content is low compared with a conventional preparation, a process for producing the solid dispersion, and a pharmaceutical composition (or a pharmaceutical preparation) comprising the solid dispersion.

It is another object of the present invention to provide a solid dispersion realizing a compact or small size preparation, a process for producing the solid dispersion, and a pharmaceutical composition (or a pharmaceutical preparation) comprising the solid dispersion.

It is still another object of the present invention to provide a solid dispersion enhancing or improving a solubility of an active ingredient even by subjecting the solid dispersion to compression molding, a process for producing the solid dispersion, and a pharmaceutical composition (or a pharmaceutical preparation) comprising the solid dispersion.

It is a further object of the present invention to provide processes for producing a solid dispersion and a pharmaceutical composition comprising the solid dispersion with a simple and easy manner.

Means to Solve the Problems

The inventors of the present invention made intensive studies to achieve the above objects and finally found that use of a specific porous silicon-containing carrier as a porous carrier in a solid dispersion containing an active ingredient hardly soluble in water (e.g., a fibrate compound) remarkably improves the solubility (or dissolution rate) and bioavailability of the active ingredient without a treatment with a supercritical fluid or the like, even by subjecting the solid dispersion to compression molding. The present invention was accomplished based on the above findings and further investigations.

That is, the solid dispersion of the present invention comprises an active ingredient having a low water solubility (or an active ingredient hardly or sparingly soluble in water) and a powdery porous carrier impregnated with and supporting the active ingredient, and the porous carrier comprises a porous silicon-containing carrier having a small heating loss in weight at a temperature of 950° C. for 2 hours. That is, the porous silicon-containing carrier has a lowered concentration of silanol group due to a surface-treatment with an organic or inorganic coupling agent or a heat-treatment such as baking. For example, the weight loss (ignition loss) of the porous silicon-containing carrier is not more then 4% by weight (e.g., not more than 3.5% by weight and particularly not more than 3.0% by weight) when the carrier is dried for removal of moisture and then heated at a temperature of 950° C. for 2 hours in accordance with Japanese Pharmacopoeia 2.43 "Loss on Ignition Test" or other test methods. The powdery porous carrier is not particularly limited to a specific one as long as the carrier at least comprises a porous silicon-containing carrier having the above-mentioned characteristics. Moreover, the solid dispersion is prepared without treatment with a supercritical fluid or a subcritical fluid. Further, the solid dispersion of the present invention can be obtained without spraying the porous carrier with a molten solid dispersion containing the active ingredient in the form of molecule or fine particle dissolved or dispersed in a matrix component. The active ingredient may be supported on or to (supported by) the porous carrier by impregnation and is usually supported on or to (supported by) the porous carrier uniformly. The porous silicon-containing carrier having the heating weight loss characteristics may comprise a spherical porous silicon-containing carrier. The porous silicon-containing carrier may be a baked silica (a fumed silica). The porous silicon-containing carrier having the heating weight loss characteristics satisfies at least one of the following intensity ratios in an infrared absorption spectrum:

(1-2) intensity ratio ($I_2/I_0$): 8 to 18
(1-3) intensity ratio ($I_3/I_0$): 10 to 40
(1-4) intensity ratio ($I_4/I_0$): 15 to 70
(1-5) intensity ratio ($I_5/I_0$): 20 to 95
(1-6) intensity ratio ($I_6/I_0$): 15 to 75
(1-7) intensity ratio ($I_7/I_0$): 10 to 45
(1-8) intensity ratio ($I_8/I_0$): 8 to 25
(2-2) intensity ratio ($I_4/I_1$): 6 to 10.5
(2-3) intensity ratio ($I_5/I_1$): 7 to 15
(2-4) intensity ratio ($I_6/I_1$): 6.5 to 12
(2-5) intensity ratio ($I_7/I_1$): 3.5 to 6.7
(3-1) intensity ratio ($I_4/I_2$): 3 to 3.9
(3-2) intensity ratio ($I_5/I_2$): 3.5 to 5.6
(3-3) intensity ratio ($I_6/I_2$): 3 to 4.5 where $I_0$ is an absorption intensity at a wave number of 3800 cm$^{-1}$, $I_1$ is that of 3650 cm$^{-1}$, $I_2$ is that of 3600 cm$^{-1}$, $I_3$ is that of 3550 cm$^{-1}$, $I_4$ is that of 3500 cm$^{-1}$, $I_5$ is that of 3450 cm$^{-1}$, I$_6$ is that of 3400 cm$^{-1}$, I$_7$ is that of 3350 cm$^{-1}$, I$_8$ is that of 3300 cm$^{-1}$, I$_9$ is that of 3200 cm$^{-1}$, and I$_{10}$ is that of 3100 cm$^{-1}$.

The porous silicon-containing carrier may have a mean pore size of 5 to 40 nm (e.g., 10 to 40 nm) and an oil absorption of 75 to 500 ml/100 g (e.g., 175 to 500 ml/100 g) in accordance with JIS (Japanese Industrial Standard) K5101. Further, the porous silicon-containing carrier may have a mean particle size of 1 to 50 μm in accordance with a laser diffraction method and a specific surface area of 250 to 1200 m$^2$/g in accordance with a BET method, and a pore volume of 0.5 to 5 ml/g. The porous silicon-containing carrier may comprise a spherical silica having a heating loss of not more than 3.0% by weight at (or after a heating of) a temperature of 950° C. for 2 hours, an oil absorption of 200 to 400 ml/100 g, and a specific surface area of 300 to 1000 m$^2$/g. The porous silicon-containing carrier may comprise a monodisperse particle and has a number of pores having a nanometer size (or unit) inside the particle, and in the carrier a void space occupies 50 to 85% of the volume of the particle. The porous silicon-containing carrier may have a sedimentation volume (an apparent specific gravity) of 10 to 50 ml/5 g in a static or stationary method. The porous silicon-containing carrier may be a spherical silica (for example, a spherical silicon dioxide). Further, the porous carrier may comprise the porous silicon-containing carrier having the heating weight loss characteristics alone or comprise a first porous silicon-containing carrier having the heating weight loss characteristics and a second porous carrier. The ratio of the first porous silicon-containing carrier relative to the second porous carrier [the former/the latter] may be, for example, about 50/50 to 100/0 (weight ratio).

The active ingredient may be a physiologically active ingredient or a pharmacologically active ingredient. The pharmacologically active ingredient may include a hypolipidemic agent, a hypertension-treating agent, an antiobesity agent, a diuretic agent, an antithrombolic agent, a diabetic agent, an agent for treating diabetic complication, and others. The pharmacologically active ingredient may be a fibrate compound, for example, at least one member selected from the group consisting of bezafibrate, clinofibrate, clofibrate, fenofibrate, beclobrate, binifibrate, ciprofibrate, etofibrate, gemfibrozil, nicofibrate, pirifibrate, ronifibrate, symfibrate, simfibrate, theofibrate, a free acid thereof, an active metabolite thereof, and a salt of these components (the fibrate compound, the free acid, and the active metabolite). The supported amount of the active ingredient may be about 0.01 to 5 parts by weight relative to 1 part by weight of the powdery porous carrier.

In the solid dispersion of the present invention, the crystalline active ingredient may be supported to the porous carrier in the form of a crystal, semicrystal, or amorphous. The crystalline active ingredient is practically supported on or to the porous carrier in the form of an amorphous.

Further, in addition to the active ingredient, a water-soluble additive component may further be supported on or to (supported by) the porous carrier. In addition to the active ingredient, at least one additive component selected from the group consisting of a water-soluble polymer, a saccharide, a surfactant, and a lipid may also be supported on or to the porous carrier. The additive component may comprise at least one member selected from the group consisting of a homo- or copolymer of vinylpyrrolidone, a polyvinyl alcohol, a homo- or copolymer of acrylic acid, a polyethylene glycol, a cellulose ether, a saccharide, a sugar alcohol, an anionic surfactant, and a nonionic surfactant. Further, the ratio of each additive component relative to 100 parts by weight of the hardly water-soluble active ingredient may be about 1 to 30 parts by weight. The total amount of the additive component may be about 1 to 50 parts by weight (e.g., about 3 to 50 parts by weight and particularly about 5 to 30 parts by weight) relative to 100 parts by weight of the hardly water-soluble active ingredient. The hardly water-soluble active ingredient and the additive component (water-soluble additive component) are usually uniformly supported throughout the porous carrier by impregnation.

According to the process of the present invention, a solid dispersion comprising a powdery porous carrier and an active ingredient hardly soluble in water supported to the powdery porous carrier is produced without a treatment with a supercritical fluid (e.g., a supercritical carbon dioxide fluid) or a subcritical fluid (e.g., a subcritical carbon dioxide fluid). In this process, a powdery porous carrier comprising a porous silicon-containing carrier having the heating weight loss characteristics is impregnated with a solution containing the active ingredient and an organic solvent (a solution in the form of a liquid at a room temperature, particularly, at a temperature of 10° C.) and the organic solvent is removed from the mixture, whereby the solid dispersion comprising the porous carrier and the active ingredient supported on or to the porous carrier can be produced. The solution containing the organic solvent may contain at least one component selected from the group consisting of a water-soluble polymer, a saccharide, and a surfactant. The solution containing the organic solvent is usually in the form of a liquid at a temperature of 10° C., and the powdery porous carrier may be impregnated with the solution by immersing the powdery porous carrier in the solution at a room temperature, and the organic solvent may be removed by drying the mixture. More specifically, the solid dispersion can be produced by spray-drying a mixture of the powdery porous carrier and the solution containing the organic solvent and the active ingredient.

The present invention also includes a pharmaceutical composition comprising the solid dispersion. The pharmaceutical composition may comprise a plurality of active ingredients, and at least one active ingredient may be a hardly water-soluble active ingredient (an active ingredient sparingly soluble in water). Such a pharmaceutical composition may comprise at least a hardly (or sparingly) water-soluble active ingredient supported on or to (supported by) a powdery porous carrier comprising a porous silicon-containing carrier having the heating weight loss characteristics. Moreover, the pharmaceutical composition may contain a first active ingredient to be administered with a higher dose (hereinafter may be referred to as a higher-dose active ingredient) and a second active ingredient to be administered with a lower dose (hereinafter may be referred to as a lower-dose active ingredient), and at least the first active ingredient may have a low water solubility (or may be sparingly soluble in water). An active ingredient having a low water solubility contained in the pharmaceutical composition may be supported on or to the powdery porous carrier. For example, the pharmaceutical composition may contain a fibrate compound and a statin-series compound, and at least the fibrate compound may be supported on or to a powdery porous carrier comprising a porous silicon-containing carrier having the heating weight loss characteristics. The pharmaceutical composition may further contain at least one additive component selected from the group consisting of an excipient, a binder, a disintegrant, and a lubricant. In the present invention, use of the above-mentioned solid dispersion does not deteriorate the solubility of the active ingredient even though the solid dispersion is subjected to the compression molding. Therefore, the preferred pharmaceutical composition is a compression-molded preparation (a solid preparation) comprising the solid dispersion. The process of the present invention comprises at least a step for compressing the solid dispersion to give the pharmaceutical composition.

Incidentally, in this specification, the term "solid dispersion" means a dispersion containing a solid porous carrier as a porous matrix and an active ingredient supported on or to (supported by) the carrier in the form of a dispersed fine particle or molecule, and the "solid dispersion" does not include a meltable dispersion (solid dispersion) which has an active ingredient in the form of a fine particle or molecule dissolved or dispersed in a meltable organic solid matrix (non-porous matrix) and is supported on or to a solid porous carrier. In this specification, a porous silicon-containing carrier having the above-mentioned heating weight loss characteristics may simply be referred to as a "first porous carrier", and another porous carrier may simply be referred to as a "second porous carrier".

Effects of the Invention

Since the present invention uses the first porous carrier (specific porous silicon-containing carrier) as a porous carrier for a solid dispersion, a solubility (or dissolution rate) or dispersibility of an active ingredient having a low solubility in water can be significantly improved and a bioavailability of the active ingredient is drastically improved in spite of the fact that the active ingredient content is low compared with a conventional preparation. Moreover, use of the first porous carrier realizes a compact or small size preparation (pharmaceutical composition or pharmaceutical preparation) to improve the patient compliance. Further, even when the solid dispersion is compressed for molding, the solubility of the active ingredient can be remarkably improved. Moreover, according to the present invention, a solid dispersion and a pharmaceutical composition comprising the solid dispersion can be produced with easy manners such as impregnation and drying without a treatment with a supercritical fluid (e.g., a supercritical carbon dioxide fluid) or a subcritical fluid (e.g., a subcritical carbon dioxide fluid).

DETAILED DESCRIPTION OF THE INVENTION

Solid Dispersion

Figure 1:
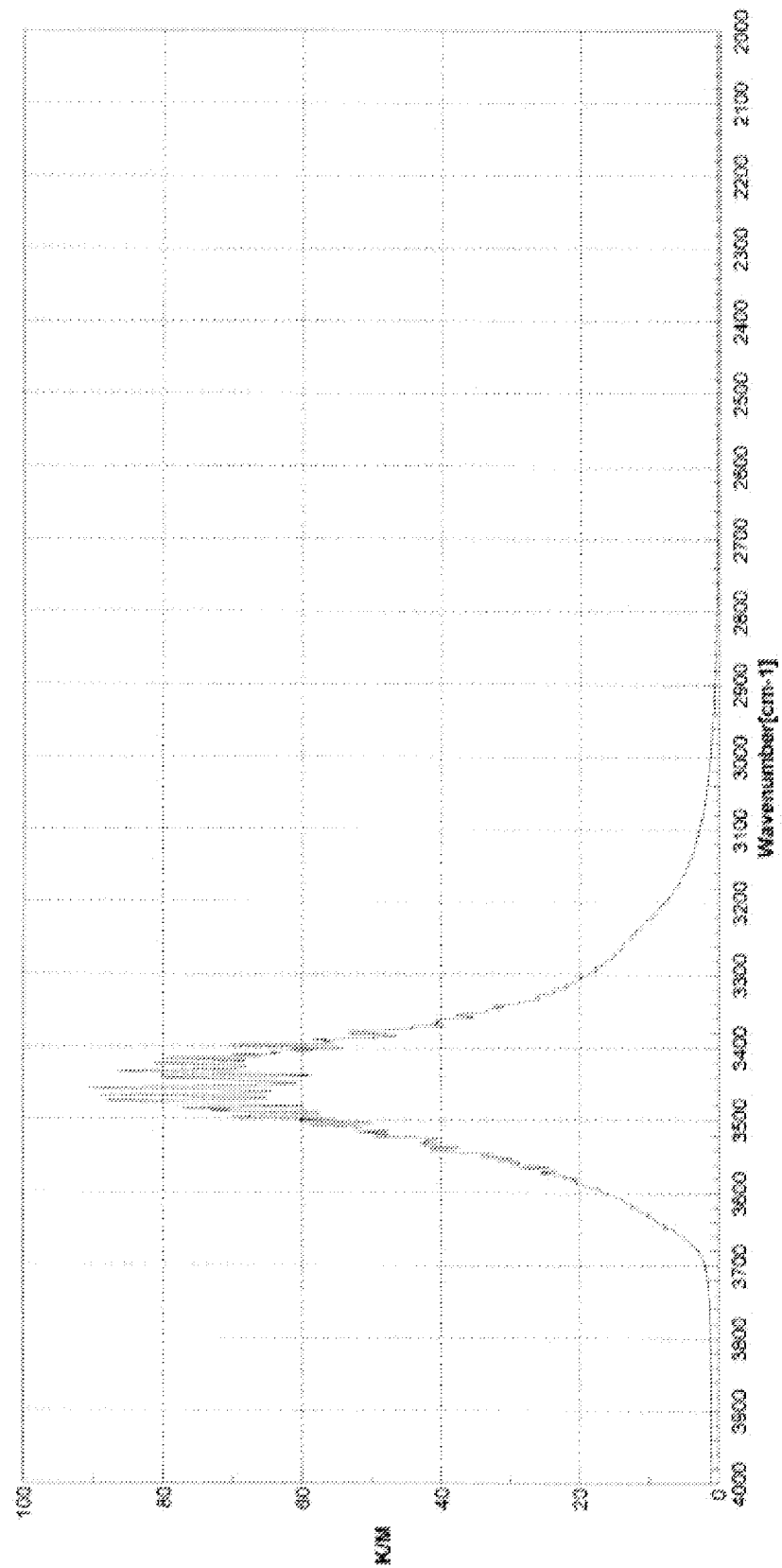
FIG. 1 represents an infrared absorption spectrum of the first porous carrier used in Examples 1 to 7.

The solid dispersion of the present invention comprises an active ingredient hardly (or sparingly) soluble in water and a powdery porous carrier impregnated with and supporting the active ingredient. The active ingredient is usually supported on the powdery porous carrier as a porous matrix by impregnation (or immersion) or permeation (or penetration) and uniformly supported throughout the powdery porous carrier. Moreover, the solid dispersion of the present invention is prepared without treating a composition containing an active ingredient hardly (or sparingly) soluble in water and a powdery porous carrier with a supercritical fluid (e.g., a supercritical carbon dioxide fluid) or a subcritical fluid (e.g., a subcritical carbon dioxide fluid) and prepared without heat-melting a meltable dispersion (a solid dispersion) having an active ingredient in the form of fine particle dispersed or molecule dissolved in a meltable organic solid matrix and spraying the solid porous carrier with the molten solid dispersion to give the solid dispersion supported on the porous carrier. Incidentally, the solubility of the active ingredient hardly soluble in water at a temperature of 25° C. is not more than 1 mg/mL, preferably not more than 0.1 mg/mL, and more preferably not more than 0.01 mg/mL.

The active ingredient may have a physiological activity or a pharmacological activity. The species of the active ingredient is not particularly limited to a specific one, and may include, for example, a hypolipidemic agent, an angina-treating agent, a hypertension-treating agent, a hypotension-treating agent, an antiobesity agent, an agent for treating heart failure, an agent for treating myocardial infarction, an antiarrhythmic agent, a diabetic agent, an agent for treating diabetic complication, an agent for treating peptic ulcer, a febrifuge, an analgesic, an antiphlogistic, a stomachic, a digestant, an antacid, an antiemetic, an antitussive expectorant, an agent for treating bronchial asthma, a constipation-treating agent, a diarrhea-treating agent (or an antidiarreheal), an agent for treating hepatic disease, an agent for treating biliary tract and spleen system, a hemorrhoid-treating agent, an agent for treating thyroid disease, an hyperlithuria-treating agent, a rheumatism-treating agent (or an antirheumatic), an antibiotic, an antidepressant, an antiallergic agent, an antituberculous agent, a prostatomegaly-treating agent, an osteoporosis-treating agent, and an agent for treating Alzheimer's disease.

The hypolipidemic agent may include an HMG-CoA reductase inhibitor, for example, a statin-series compound such as simvastatin, lovastatin, atorvastatin, pitavastatin, rosuvastatin, cerivastatin, itavastatin, ZD-4522, or a salt thereof (e.g., a sodium salt and a calcium salt), a fibrate compound, probucol, a nicotinic acid-series agent (e.g., nicomol and niceritrol), ethyl icosapentate, and a plant sterol (e.g., soysterol), a small intestine cholesterol transporter inhibitor (e.g., ezetimibe), and an anion exchange resin (colestimide, cholestyramine).

The hypertension-treating agent may include, for example, an angiotensin converting enzyme inhibitor (e.g., temocapril, cilazapril, trandolapril, or a salt thereof), an angiotensin II antagonist (e.g., candesartan cilexetil, eprolosartan, valsartan, telmisartan, irbesartan, olmesartan medoxomil, tasosartan, or a salt thereof), a calcium antagonist (e.g., manidipine, nifedipine, nicardipine, amlodipine, efonidipine, or a salt thereof), a potassium channel opener (e.g., levcromakalim), clonidine hydrochloride, and bunazosin hydrochloride.

The antiobesity agent may include, for example, a central antiobesity agent (e.g., dexfenfluramine, fenfluramine, phentermine, sibutramine, amfepramone, dexamphetamine, mazindol, phenylpropanolamine, and clobenzorex), a pancreatic lipase inhibitor (e.g., orlistat), a β3 agonist, a peptidergic anorectic (e.g., leptin, CNTF (ciliary neurotrophic factor)), and a cholecystokinin agonist (e.g., lintitript).

The agent for treating heart failure may include, for example, a xanthine derivative (e.g., sodium salicylate and theobromine, and calcium salicylate and theobromine), a thiazide-series compound (e.g., ethiazide, cyclopenthiazide, trichlormethiazide, hydrochlorothiazide, hydroflumethiazide, benzylhydrochlorothiazide, penflutizide, polythiazide, and methyclothiazide), a non-thiazide-series compound (e.g., meticrane and tripamide), an aldosterone antagonist-series compound (e.g., spironolactone and triamterene), a carbonic anhydrase inhibitor (e.g., acetazolamide), a chlorobenzene-sulfonamide-series compound (e.g., chlortalidone, mefruside, and indapamide), azosemide, isosorbide, ethacrynic acid, piretanide, bumetanide, and furosemide.

The agent for treating myocardial infarction may include, for example, a heparin (e.g., heparin sodium, heparin calcium, and dalteparin sodium), a warfarin, an antithrombin agent (e.g., aragatroban), a thrombolytic agent (e.g., urokinase, tisokinase, alteplase, nateplase, monteplase, and pamiteplase), a platelet aggregate inhibitor (e.g., dipyridamole, cilostazol, and ethyl icosapentate), and aspirin.

The diabetic agent may include, for example, an insulin preparation, an α-glucosidase inhibitor (e.g., voglibose and acarbose), abiguanide agent (e.g., phenformin or a salt thereof), an insulin secretagogue [for example, a sulfonylurea agent (e.g., tolbutamide, glibenglamide, gliclazide, chlorpropamide, tolazamide, acetohexamide, glyclopyramide, glimepiride, glipizide, and glybuzole), repaglinide, nateglinide, mitiglinide, or a calcium salt hydrate thereof], a dipeptidylpeptidase IV inhibitor, a β3 agonist, an amylin agonist (e.g., pramlintide), a phosphotyrosine phosphatase inhibitor (e.g., vanadic acid), a glyconeogenesis inhibitor (e.g., a glycogen phosphorylase inhibitor, a glucose-6-phosphatase inhibitor, and a glucagon antagonist), a SGLUT (sodium-glucose cotransporter) inhibitor (e.g., T-1095), and an insulin resistance improving agent (e.g., pioglitazone hydrochloride).

The agent for treating diabetic complication may include, for example, an aldose reductase inhibitor (e.g., tolrestat, epalrestat, zenarestat, zopolrestat, minalrestat, and fidarestat), a neurotrophic factor (e.g., NGF and NT-3), a neurotrophic factor production•secretion accelerator, a PKC inhibitor, an AGE inhibitor, an active oxygen scavenger (e.g., thioctic acid), and a carebral vasodilator.

The agent for treating peptic ulcer may include, for example, a proton pump inhibitor (e.g., omeprazole and lansoprazole), and a defensive factor enhancing agent (e.g., teprenone, metoclopramide, and sofalcone).

The rheumatism-treating agent may include, for example, an immunosuppressant (e.g., leflunomide and methotrexate), salazosulfapyridine, and auranofin.

The antiallergic agent may include, for example, an antihistamine (e.g., clemastine fumarate, loratadine, mequitazine, ebastine, oxatomide, pranlukast hydrate, and bepotastine besilate).

Further, if necessary, a crude drug (or a galenical), a vitamin compound (e.g., vitamin A, vitamin B, vitamin $B_{12}$ (mecobalamin), vitamin C, vitamin D, and vitamin B), a mineral compound, an amino acid compound, or others may be used.

These active ingredients may be either an optically active substance or a racemic body (or racemate). These active ingredients may be used singly or in combination.

In the pharmacologically active ingredients, the above-mentioned fibrate compound may include, for example, bezafibrate, clinofibrate, clofibrate, fenofibrate, beclobrate, binifibrate, ciprofibrate, etofibrate, gemfibrozil, nicofibrate, pirifibrate, ronifibrate, symfibrate, simfibrate, theofibrate, or a salt thereof (e.g., clofibrate aluminum). The fibrate compound also includes a derivative of an active compound (e.g., an ester, a salt hydrate, and a hydrate), a prodrug, a free acid, or an active metabolite (e.g., fibric acid, clofibric acid, and fenofibric acid), or a salt of these components. For example, the fibrate compound may be fenofibrate and a free acid or active metabolite (fenofibric acid) corresponding to fenofibrate.

The fibrate compound may be either an optically active substance or a racemic body. These fibrate compounds may be used singly or in combination. Moreover, the fibrate compound may be used in combination with other active ingredients [for example, at least one member selected from the group consisting of other agents for treating hyperlipemia excluding the fibrate compound (e.g., an HMG-CoA reductase inhibitor (a statin-series compound)), a hypertension-treating agent, an antiobesity agent, a diuretic agent, an antithrombolic agent, a diabetic agent, and an agent for treating diabetic complication].

The fibrate compound decreases a low-density lipoprotein-associated (LDL) cholesterol and a triglyceride (TG) by inhibiting triglyceride synthesis or secretion in the liver, and in addition, increases a high-density lipoprotein-associated (HDL) cholesterol. The fibrate compound is useful for a prophylactic or therapeutic agent for hyperlipemia (or an agent for preventing and/or treating for hyperlipemia). Among the fibrate compounds, fenofibrate, having a lipid-lowering function, particularly, a function or action for greatly decreasing an LDL cholesterol or a triglyceride, is preferred.

Further, the active ingredient may be either amorphous or crystalline. Even when the ingredient is a crystalline, the solubility of the ingredient can be remarkably improved in the solid dispersion of the present invention. Therefore, even in a small amount of the active ingredient, the bioavailability can be greatly improved.

According to the present invention, the dosage form of the preparation can be made compact or small even when an active ingredient has a low solubility (or dissolution rate) and a low bioavailability and the dose to be administered of the ingredient is high. Moreover, the bioavailability of the preparation can be improved even when the dose is reduced. Therefore, the present invention is preferably applied to an active ingredient having a low solubility in water and a low bioavailability. The present invention may be applied to an active ingredient to be administered with a low dose (for example, to be administered with a single dose of about 0.1 to 15 mg, preferably about 0.5 to 10 mg, and more preferably about 1 to 5 mg). In particular, the present invention is preferably applied to an active ingredient having a low solubility in water and a low bioavailability, to be administered with a high dose (for example, to be administered with a single dose of about 25 to 1000 mg, preferably about 30 to 500 mg, and more preferably about 50 to 300 mg). Such an active ingredient to be administered with a high dose may include a hypolipidemic agent (for example, a fibrate compound (e.g., fenofibrate), probucol, and a nicotinic acid-series agent), an antiobesity agent, an agent for treating heart failure, an agent for treating myocardial infarction, a diabetic agent, an agent for treating diabetic complication, and others. The weight ratio of the higher-dose active ingredient relative to the lower-dose active ingredient (the former/the latter) may be, for example, about 1000/1 to 5/1, preferably about 500/1 to 10/1, and more preferably about 300/1 to 20/1 (e.g., about 100/1 to 25/1), and may be about 20/1 to 5/1.

Incidentally, in the present invention, a plurality of active ingredients may be supported on (supported by) the porous carrier. For example, both of the higher-dose active ingredient (e.g., a fibrate compound such as fenofibrate) and the lower-dose active ingredient (e.g., a statin-series compound such as pitavastatin (or pitavastatin calcium)) may be supported on the porous carrier.

Further, the above-mentioned hardly soluble active ingredient may be supported on the porous carrier in the solid dispersion. The hardly soluble active ingredient and the water-soluble active ingredient may be supported on the porous carrier.

The present invention uses a powdery porous carrier comprising a porous silicon-containing carrier (the first porous carrier) having a heating loss of not more than 4% by weight at a temperature of 950° C. for 2 hours. That is, the powdery porous carrier comprises at least the first porous carrier (porous silicon-containing carrier) having the heating weight loss characteristics. The first porous carrier may comprise an inorganic silicon compound, for example, a silicon oxide (e.g., a silicon dioxide, a hydrated silicon dioxide, and a silica), a silic acid compound [for example, a silic acid (e.g., a light anhydrous silic acid) and a salt of a silic acid (e.g., calcium silicate, magnesium silicate, aluminum silicate, magnesium aluminum silicate, magnesium aluminosilicate, and magnesium aluminometasilicate)]. These first porous carriers may be used singly or in combination. These first porous carriers practically comprise a silicon dioxide (including a hydrated silicon dioxide) or a silica.

The silicon-containing carrier may be an untreated one or may have a silanol group (e.g., about 2 to 5.5% by weight (preferably about 2.5 to 5% by weight) of a silanol group relative to the total weight of the carrier). Incidentally, since a carrier having a large number of silanol groups improves the binding capacity (moldability) by compression molding, such a carrier is suitable for an excipient. However, the compression molding of the carrier having a high binding capacity remarkably suppresses the solubility of the active ingredient. Accordingly, the silicon-containing carrier may be, for example, a carrier in which the silanol group concentration is reduced or adjusted to about 0.5 to 4% by weight, preferably about 1 to 3.5% by weight, and more preferably about 1.5 to 3% by weight (e.g., about 1.5 to 2.5% by weight) relative to the total weight of the carrier. In order to reduce the binding strength of the porous silicon-containing substance in the compression-molding, the silicon-containing carrier may be surface-treated with a surface-treating agent (or a finishing agent) or a surface-improving agent (e.g., a coupling agent) and/or heat-treated by baking or other means to reduce or adjust the silanol group concentration.

The surface-treating agent or surface-improving agent may be an organic coupling agent (e.g., an organic acid such as an organic carboxylic acid, an acid anhydride thereof, or an acid halide thereof; a (poly)isocyanate compound such as an aliphatic (poly)isocyanate or an aromatic (poly)isocyanate; a (poly)amine such as an aliphatic (poly)amine or an aromatic (poly)amine; and an epoxy compound), or an inorganic coupling agent. The inorganic coupling agent may include, for example, a silane coupling agent such as an alkoxysilane [e.g., a tetra$C_{1-4}$alkoxysilane such as tetramethoxysilane or tetraethoxysilane, a mono$C_{1-4}$alkyltri$C_{1-4}$alkoxysilane such as methyltrimethoxysilane or ethyltriethoxysilane, a di$C_{1-4}$alkyldi$C_{1-4}$alkoxysilane such as dimethyldimethoxysilane or diethyldiethoxysilane, and a tri$C_{1-4}$alkylmono$C_{1-4}$alkoxysilane such as trimethylmonomethoxysilane or triethylmonoethoxysilane]; an arylalkoxysilane [e.g., a monoaryltri$C_{1-4}$alkoxysilane such as phenyltrimethoxysilane or phenyltriethoxysilane, and a diaryldi$C_{1-4}$alkoxysilane such as diphenyldimethoxysilane or diphenyldiethoxysilane]; an alkoxysilane having a haloalkyl group, such as 3-chloropropyltriethoxysilane; an alkoxysilane having a mercapto group, such as 3-mercaptopropyltrimethoxysilane or 3-mercaptopropyltriethoxysilane; an alkoxysilane having a carboxyl group, such as 2-carboxyethyltrimethoxysilane or 3-carboxypropyltriethoxysilane; an alkoxysilane having an amino group or a substituted amino group, such as 3-aminopropyltrimethoxysilane or 3-aminopropyltriethoxysilane; an alkoxysilane having an epoxy group, such as glycidyloxyethyltrimethoxysilane, glycidyloxypropyltriethoxysilane, or cyclohexene oxide ethyltrimethoxysilane; an alkoxysilane having a vinyl group or a (meth)acryloyl group, such as 3-(meth)acryloxypropyldimethylmethoxysilane; an alkoxysilane having a hydroxyl group, such as 2-(2-hydroxyethoxy)ethyltrimethoxysilane, 3-(2-hydroxyethoxy)propyltrimethoxysilane, an adduct having an alkylene oxide (e.g., ethylene oxide) added to a hydroxyl group thereof; or a halosilane in which at least part of alkoxy groups in the alkoxysilane is replaced with a halogen atom (a chlorine or bromine atom) (e.g., dimethylchloromethoxysilane). The inorganic coupling agent may be aluminum coupling agents, titanium coupling agents, zirconium coupling agents, and the like, each corresponding to these silane coupling agents. The amount of the surface-treating agent may be selected from the range that does not deteriorate the moldability. Moreover, the amount to be used of the surface-treating agent can be evaluated from an infrared absorption spectrum as an index.

The heat-treatment such as baking can be carried out in an atmosphere of an oxygen-containing gas (e.g., air), an inactive gas (e.g., nitrogen gas, a rare gas such as helium gas or argon gas, and carbon dioxide gas), hydrogen gas, or others at a temperature of about 500 to 2000° C. (preferably about 800 to 1700° C. and more preferably about 1000 to 1500° C.). The heat treatment time may be, for example, about 10 minutes to 24 hours (e.g., about 30 minutes to 12 hours and particularly about 1 to 6 hours). The heat treatment allows a dehydration reaction of a silanol group to proceed, thereby reducing the concentration of silanol group. Therefore, the first porous carrier may be a baked silica (a fumed silica). Moreover, the first porous carrier may be granulated. For the granulation, a conventional granulating manner such as tumbling granulation or fluidized bed granulation may be utilized. The granulation may be conducted together with the above-mentioned surface treatment and/or heat treatment.

The first porous carrier may have a heating loss (ignition loss) of not more than 4% by weight (preferably not more than 3.5% by weight, more preferably not more than 3.0% by weight, particularly not more than 2.5% by weight, for example, not more than 2% by weight) at a temperature of 950° C. for 2 hours. For example, the heating loss (ignition loss) may be about 0.3 to 3.5% by weight (e.g., about 0.5 to 3% by weight) or may be about 0 to 2.5% by weight (e.g., about 0 to 2% by weight). Such a heating loss (ignition loss) can be measured by drying (drying at 105° C. over 2 hours) for removal of moisture (e.g., an absorbed water), then heating the dried matter at a temperature of 950° C. for 2 hours in accordance with Japanese Pharmacopoeia 2.43 "Loss on Ignition Test" or other test methods, and calculating the weight loss of the carrier after heating.

The first porous carrier is not particularly limited to a specific one as long as the carrier is in the form of particulate. The form (or shape) of the first porous carrier may be amorphous, spherical, ellipsoidal, polyhedral, prismatic, or others. The form (or shape) is usually spherical or ellipsoidal (particularly, spherical). Use of the first spherical porous carrier can reduce a preparation size due to a high flowability and a small bulk density and can improve handleability and workability of a preparation process including a tablet compression (or tableting) step.

The first porous carrier (silicon-containing carrier) usually shows an absorption peak at a wave number of 3400 to 3500 cm$^{-1}$ (for example, a wave number of 3440 to 3480 cm$^{-1}$) in an infrared absorption spectrum. Incidentally, depending on the measuring conditions, the absorption intensity may fluctuate at the above-mentioned wave number range. The first porous carrier has a characteristic that the absorption intensity is lower, as compared with a light anhydrous silic acid, at a range of at least a wave number of 3100 to 3550 cm$^{-1}$, particularly 3200 to 3400 cm$^{-1}$ (e.g., 3300 to 3350 cm$^-$) in an infrared absorption spectrum.

When an absorption intensity at a wave number of 3800 cm$^{-1}$ is defined as $I_0$, that of 3650 cm$^{-1}$ is defined as $I_1$, that of 3600 cm$^{-1}$ is defined as $I_2$, that of 3550 cm$^{-1}$ is defined as $I_3$, that of 3500 cm$^{-1}$ is defined as $I_4$, that of 3450 cm$^{-1}$ is defined as $I_5$, that of 3400 cm$^{-1}$ is defined as $I_6$, that of 3350 cm$^{-1}$ is defined as $I_7$, that of 3300 cm$^{-1}$ is defined as $I_8$, that of 3200 cm$^{-1}$ is defined as $I_9$, and that of 3100 cm$^{-1}$ is defined as $I_{10}$, in an infrared absorption spectrum of the first porous carrier, at least one intensity ratio may be as follows.

(1) Intensity Ratio Relative to the Absorption Intensity $I_0$ (1-1) Intensity ratio ($I_1/I_0$): about 1 to 7 (e.g., about 2 to 6.7), preferably about 3 to 6.5 (e.g., about 3.5 to 6.5), more preferably about 3.7 to 6.3 (e.g., about 4 to 6.2), and particularly about 4.5 to 6.3 (e.g., about 5 to 6.2)

(1-2) Intensity ratio ($I_2/I_0$): about 1 to 19 (e.g., about 2 to 18.5, particularly about 5 to 18.5), preferably about 8 to 18 (e.g., about 8.5 to 17.5), more preferably about 9 to 17 (e.g., about 9.2 to 16.7), and particularly about 10 to 18 (e.g., about 11 to 17)

The above-mentioned intensity ratio ($I_2/I_0$) may be as follows. Intensity ratio ($I_2/I_0$): about 1 to 6, preferably about 2 to 5 (e.g., about 2.5 to 4.5), more preferably about 2.8 to 4.2 (e.g., about 3 to 4), and particularly about 3.5 to 4

(1-3) Intensity ratio ($I_3/I_0$): about 2.5 to 42 (e.g., about 7.5 to 40), preferably about 10 to 40 (e.g., about 12 to 38), more preferably about 15 to 37 (e.g., about 17 to 35), usually about 20 to 40 (e.g., about 22 to 37), and particularly about 23 to 36

(1-4) Intensity ratio ($I_4/I_0$): about 3 to 75 (e.g., about 10 to 70), preferably about 15 to 70 (e.g., about 20 to 65), more preferably about 25 to 62 (e.g., about 27 to 61), usually about 30 to 75 (e.g., about 35 to 73), and particularly e.g., about 38 to 70

The intensity ratio ($I_4/I_0$) may be as follows. Intensity ratio ($I_4/I_0$): about 3 to 15 (e.g., about 4 to 12), preferably about 4.5 to 10 (e.g., about 5 to 10), more preferably about 5.5 to 9 (e.g., about 6 to 8.5), and particularly about 6.5 to 8

(1-5) Intensity ratio ($I_5/I_0$): about 5 to 105 (e.g., about 10 to 100), preferably about 20 to 95 (e.g., about 25 to 90), more preferably about 30 to 87 (e.g., about 35 to 86), usually about 40 to 110 (e.g., about 45 to 105), and particularly about 50 to 100

(1-6) Intensity ratio ($I_6/I_0$): about 3.5 to 75 (e.g., about 10 to 75), preferably about 15 to 75 (e.g., about 20 to 73), more preferably about 25 to 72 (e.g., about 28 to 70), usually about 35 to 85 (e.g., about 40 to 80), and particularly about 45 to 75

The intensity ratio ($I_6/I_0$) may be as follows. Intensity ratio ($I_6/I_0$): about 3.5 to 20 (e.g., about 4 to 15), preferably about 4.5 to 13 (e.g., 5 to 12), more preferably about 5.5 to 10 (e.g., about 6 to 9), and particularly about 6.5 to 8.5

(1-7) Intensity ratio ($I_7/I_0$): about 2.5 to 47 (e.g., about to 45), preferably about 10 to 45 (e.g., about 12 to 42), more preferably about 15 to 40 (e.g., about 18 to 38), usually about 20 to 50 (e.g., about 23 to 47), and particularly about 25 to 45

(1-8) Intensity ratio ($I_8/I_0$): about 1.5 to 27 (e.g., about 5 to 26), preferably about 8 to 25 (e.g., about 9 to 23), more preferably about 10 to 22 (e.g., about 11 to 21), usually about 13 to 30 (e.g., about 14 to 27), and particularly about 15 to 25

The intensity ratio ($I_8/I_0$) may be as follows. Intensity ratio ($I_8/I_0$): about 1.5 to 10 (e.g., about 2 to 8), preferably about 2.5 to 7 (e.g., about 3 to 6), and more preferably about 3.5 to 5.5 (e.g., about 4 to 5)

(1-9) Intensity ratio ($I_9/I_0$): about 1 to 12 (e.g., about 3 to 11), preferably about 4.5 to 10.5 (e.g., about 5 to 10), more preferably about 5.5 to 9.5 (e.g., about 5.6 to 9), usually about 6.0 to 12 (e.g., about 6.2 to 11), and particularly about 6.2 to 10

The intensity ratio ($I_9/I_0$) may be as follows. Intensity ratio ($I_9/I_0$): about 1 to 5 (e.g., about 1.5 to 4.5), preferably about 2 to 4 (e.g., about 2.5 to 3.5)

(1-10) Intensity ratio ($I_{10}/I_0$): about 0.5 to 4.5 (e.g., about 1 to 4.5), preferably about 1.2 to 4.3 (e.g., about 1.3 to 4.2), and more preferably about 1.3 to 4 (e.g., about 1.5 to 3.7)

The intensity ratio ($I_{10}/I_0$) may be as follows. Intensity ratio ($I_{10}/I_0$): about 0.5 to 3 (e.g., about 1 to 3), preferably about 1.2 to 2.5 (e.g., about 1.5 to 2.5), and particularly about 1.2 to 2.0

(2) Intensity Ratio Relative to the Absorption Intensity $I_1$ (2-1) Intensity ratio ($I_3/I_1$): about 3.5 to 5.8 (e.g., about 3.7 to 5.7), preferably about 3.8 to 5.8 (e.g., about 3.9 to 5.7), more preferably about 4 to 5.8 (e.g., about 4.2 to 5.7), and particularly about 4.5 to 5.8 (e.g., about 4.6 to 5.7)

(2-2) Intensity ratio ($I_4/I_1$): about 6 to 10.5, preferably about 6.3 to 10.3 (e.g., about 6.5 to 10.3), more preferably about 6.7 to 10.2 (e.g., about 6.8 to 10), and particularly about 7.7 to 10.5 (e.g., about 7.8 to 10)

(2-3) Intensity ratio ($I_5/I_1$): about 7 to 15, preferably about 7.5 to 14.7 (e.g., about 8 to 14.5), more preferably about 8.5 to 14.3 (e.g., about 9 to 14), usually about 9.5 to 15 (e.g., about 9.8 to 14.8), and particularly about 10 to 14.5

(2-4) Intensity ratio ($I_6/I_1$): about 6.5 to 12 (e.g., about 6.7 to 11.7), preferably about 7 to 11.5 (e.g., about 7.2 to 11.2), more preferably about 7.5 to 11.1 (e.g., about 7.5 to 11), usually about 8 to 12 (e.g., about 8.2 to 12), and particularly about 8 to 11.5

(2-5) Intensity ratio ($I_7/I_1$): about 3.5 to 6.7 (e.g., about 3.7 to 6.6), preferably about 4 to 6.5 (e.g., about 4.3 to 6.5), more preferably about 4.5 to 6.3, usually about 4.6 to 6.7 (e.g., about 4.8 to 6.6), and particularly about 4.8 to 6.5

(2-6) Intensity ratio ($I_8/I_1$): about 2.3 to 3.8 (e.g., about 2.5 to 3.7), preferably about 2.6 to 3.5 (e.g., about 2.7 to 3.5), and more preferably about 2.8 to 3.4 (e.g., about 2.9 to 3.3)

(2-7) Intensity ratio ($I_9/I_1$): about 1 to 1.7, and preferably about 1.1 to 1.6 (e.g., about 1.1 to 1.5)

(3) Intensity Ratio Relative to the Absorption Intensity $I_2$ (3-1) Intensity ratio ($I_4/I_2$): about 3 to 3.9 (e.g., about 3.2 to 3.9), preferably about 3.2 to 3.8 (e.g., about 3.1 to 3.7), and particularly about 3.3 to 3.9 (e.g., about 3.4 to 3.8)

(3-2) Intensity ratio ($I_5/I_2$): about 3.5 to 5.6, preferably about 3.7 to 5.5, more preferably about 3.8 to 5.4 (e.g., about 4 to 5.4), usually about 4.2 to 5.6 (e.g., about 4.3 to 5.5), and particularly about 4.4 to 5.4

(3-3) Intensity ratio ($I_6/I_2$): about 3 to 4.5, preferably about 3.1 to 4.4 (e.g.), more preferably about 3.2 to 4.2 (e.g., about 3.3 to 4.1), and particularly about 3.5 to 4.5 (e.g., about 3.6 to 4.3)

(3-4) Intensity ratio ($I_7/I_2$): about 1.5 to 2.5 (e.g., about 1.7 to 2.5), preferably about 1.8 to 2.5, more preferably about 1.9 to 2.4 (e.g., about 2 to 2.3), and particularly about 2.1 to 2.5

(3-5) Intensity ratio ($I_8/I_2$): about 1 to 1.4, preferably about 1.1 to 1.4, and more preferably about 1.2 to 1.3

Regarding the above-mentioned intensity ratios, (1) the intensity ratio relative to the absorption intensity $I_0$ and (2) the intensity ratio relative to the absorption intensity $I_1$ are useful for distinguishing the first porous carrier from a porous silicon-containing carrier having a high concentration of silanol group or hydroxyl group (for example, an amorphous porous carrier such as a light anhydrous silic acid). The intensity ratio (1) is preferably particularly at least one intensity ratio of the intensity ratios (1-1) to (1-10), particularly at least one intensity ratio of the intensity ratios (1-1) to (1-9), among others at least one intensity ratio of the intensity ratios (1-2) to (1-8). The intensity ratio (2) is particularly at least one intensity ratio of the intensity ratios (2-1) to (2-6), particularly at least one intensity ratio of the intensity ratios (2-2) to (2-5). Moreover, (3) the intensity ratio relative to the absorption intensity $I_2$ (particularly, at least one intensity ratio of the intensity ratios (3-1) to (3-5), particularly at least one intensity ratio of the intensity ratios (3-1) to (3-3)) may also serve as a useful index for distinguishing the first porous carrier.

Incidentally, the first porous carrier is not particularly limited to a specific one as long as the carrier satisfies at least one of the above-mentioned intensity ratios. The first porous carrier may satisfy a plurality of the above-mentioned intensity ratios (e.g., two intensity ratios such as the intensity ratio ($I_2/I_0$) and the intensity ratio ($I_3/I_0$)) or all of the above-mentioned intensity ratios.

The intensity ratio based on the infrared absorption spectrum may be calculated by mixing about 200 mg of KBr and about 2 mg of a carrier in a mortar to prepare a plate and measuring an infrared absorption spectrum of the plate to give an absorption intensity at each wave number in accordance with a KBr method. An absorption intensity at a predetermined wave number can be represented as a height from a baseline in the infrared absorption spectrum chart. For calculating the intensity ratios, a low absorption intensity value (for example, the absorption intensities $I_0$ and $I_1$) can exactly be measured by enlarging the infrared absorption spectrum. An absorption intensity value at a fluctuation range (for example, the absorption intensities $I_5$ and $I_6$) can be measured by smoothing intensities in the fluctuation range of the infrared absorption spectrum to draw a wholly smooth curve or straight line and determining an intersection of the smooth curve or straight line with the predetermined wave number.

The mean pore size of the first porous carrier is, for example, about 5 to 40 nm, preferably about 7 to 35 nm, and more preferably about 10 to 30 nm (e.g., about 15 to 25 nm). In order to improve the solubility of the active ingredient, the mean pore size of the first porous carrier is preferably large in some degree, and therefore, for example, it is advantageous that the mean pore size of the carrier is about 10 to 40 nm, preferably about 12 to 35 nm, and more preferably about 13 to 30 nm (e.g., about 15 to 25 nm).

The oil absorption (or oil absorption amount) of the first porous carrier (measured by the method defined in JIS K501, unit: ml/100 g) is, for example, about 75 to 500 (preferably about 100 to 450, more preferably about 150 to 400, particularly about 200 to 380 (e.g., about 220 to 350), and usually about 230 to 320. In order to increase the supported amount of the active ingredient and improve the solubility of the active ingredient, it is preferable that the oil absorption of the first porous carrier be high, and thus the oil absorption of the carrier is, for example, about 175 to 500 (preferably about 190 to 450, more preferably about 200 to 400, particularly about 220 to 380 (e.g., about 230 to 350), and usually about 230 to 320.

Further, the mean particle size of the first porous carrier measured by a laser diffraction method may be about 1 to 50 μm, preferably about 2 to 45 μm (e.g., about 3 to 40 μm), and more preferably about 3 to 35 μm (e.g., about 5 to 30 μm). Moreover, the mean particle size of the first porous carrier may be, for example, about 1 to 25 μm (e.g., about 7 to 25 μm), preferably about 2 to 20 μm (e.g., about 8 to 15 μm), and more preferably about 3 to 15 μm (e.g., about 9 to 13 μm) or may be about 8 to 22 μm (e.g., about 10 to 12 μm). The specific surface area of the first porous carrier measured by a BET method (unit: $m^2/g$) is, for example, about 250 to 1200 (preferably about 300 to 1000, more preferably about 350 to 900, and particularly about 400 to 800 (e.g., about 400 to 600). Moreover, the pore volume of the first porous carrier (unit: ml/g) is, for example, about 0.5 to 5 (preferably about 0.7 to 3, more preferably about 0.8 to 2.5, and particularly about 1 to 2. Further, the sedimentation volume (apparent specific gravity, unit: ml/5 g) of the first porous carrier measured by a static or stationary method is, for example, about 10 to 50 (preferably about 15 to 45, and more preferably about 20 to 40).

Further, the first porous carrier may have a number of pores having a nanometer size or unit (the above-mentioned mean pore size) inside thereof, and the void space may occupy about 50 to 85% (e.g., about 55 to 83%, preferably about 60 to 80%, and more preferably about 65 to 80% (e.g., about 70 to 80%)) of the volume of the carrier. Furthermore, the particle size distribution of the first porous carrier may be either polydisperse or monodisperse, and preferably monodisperse. In particular, regarding the first porous carrier (e.g., when a particle size in a cumulative frequency of 10% is defined as D10 and a particle size in a cumulative frequency of 90% is defined as D90 in a particle size distribution based on the volume), a monodisperse particle may have a particle size distribution width (D90/D10) of about 1.2 to 3, preferably about 1.3 to 2.7, and more preferably about 1.5 to 2.5 (e.g., about 1.85 to 2.3).

Incidentally, the pH of 5% by weight slurry of the first porous carrier in water may be about 4 to 8 (e.g., about 5 to 7).

In order to improve the solubility of the active ingredient, it is advantageous to use a carrier having a relatively large mean pore size, specific surface area, and oil absorption as the first porous carrier. The mean pore size of such a carrier is about 12 to 35 nm and preferably 13 to 30 nm (e.g., about 15 to 25 nm) or may be about 15 to 20 nm. Moreover, the BET specific surface area (unit: $m^2/g$) of the carrier is, for example, about 400 to 900 (e.g., about 450 to 850) and preferably about 500 to 800 (e.g., about 500 to 750). The oil absorption (unit: ml/100 g) of the carrier may be about 200 to 500 (e.g., about 220 to 450) and preferably about 230 to 400 (e.g., about 230 to 350) or may be about 230 to 320.

The use of such a first porous carrier (e.g., a spherical porous silica) remarkably improves the solubility and bioavailability of the active compound and realizes a compact or small size preparation probably because the carrier has a small bulk density and stably supports the active ingredient in a fine particle or molecular state. Moreover, even if the solid dispersion containing the carrier is subjected to granulation or compression-molding to obtain granules or tablets, the dissolution rate of the active ingredient from the preparation can be improved.

Incidentally, the first porous carrier is available as trade name numbers "C-1504" and "C-1510" of "SYLOSPHERE" (manufactured by Fuji Silysia Chemical Ltd.), a trade name number "300/30" of "AEROPERL" (manufactured by Degussa), and others. Moreover, the first porous carrier is available in a spherical form (a form such as a spherical porous silica).

In the solid dispersion, the form of the active ingredient is not particularly limited to a specific form, and may be in a crystalline or an amorphous form. In particular, even when the active ingredient is crystalline, the ingredient may be supported in an amorphous form on or to the first porous carrier having the heating weight loss characteristics (e.g., a spherical porous silica). That is, neither peak due to crystal nor endoergic peak is observed even in supporting the crystalline active ingredient on or to the first porous carrier having the heating weight loss characteristics (e.g., a spherical porous silica) and performing an X-ray diffraction and a thermal analysis of the supported ingredient. Accordingly, the present invention can improve the solubility of the active ingredient effectively even when a crystalline active ingredient is used.

Since the first porous carrier having the heating weight loss characteristics (e.g., a spherical porous silicon-containing carrier) functions or serves as an excipient, the powdery porous carrier may comprise the first porous carrier alone, or if necessary, may comprise the first porous carrier and a second porous carrier. The second porous carrier may include, for example, a cellulose such as a crystal cellulose (e.g., a porous cellulose), a resin (e.g., an ion exchange resin, a thermoplastic resin, and a thermosetting resin), an inorganic substance [for example, an activated carbon, a mineral (e.g., a zeolite, a diatomaceous earth, a talc, a kaolin, and a clay), a metal oxide (e.g., alumina, zinc oxide, and titanium dioxide), a metal hydroxide (e.g., an alkaline earth metal hydroxide such as calcium hydroxide; and aluminum hydroxide), a metal carbonate (e.g., an alkaline earth metal carbonate such as calcium carbonate), a metal sulfate (e.g., an alkaline earth metal sulfate such as calcium sulfate), and a metal phosphate (e.g., an alkaline earth metal phosphate such as calcium phosphate)]. These porous carriers may be used singly or in combination.

The preferred second porous carrier includes a porous silicon-containing carrier. The porous silicon-containing carrier may comprise, for example, a silicon dioxide (including a hydrated silicon dioxide) or a silica, a silic acid compound [for example, a light anhydrous silic acid, calcium silicate, magnesium silicate, aluminum silicate, magnesium aluminum silicate, magnesium aluminosilicate, synthetic sodium magnesium silicate, and colloidal hydrous aluminum silicate], a diatomaceous earth, and a zeolite. These second carriers may be used singly or in combination. The second porous carrier may be amorphous or have a spherical shape or form (including an ellipsoidal shape or others). The light anhydrous silic acid, calcium silicate, magnesium silicate, magnesium aluminum silicate, and/or magnesium aluminosilicate is practically used as the amorphous or spherical carrier. In particular, an amorphous light anhydrous silic acid is practically used as the second amorphous porous carrier. Incidentally, the amorphous light anhydrous silic acid is available as, for example, SYLYSIA Series (e.g., SYLYSIA 250, SYLYSIA 320, SYLYSIA 350, SYLYSIA 470, SYLYSIA 440, and SYLYSIA 740) manufactured by Fuji Silysia Chemical Ltd., ADSOLIDER Series (e.g., ADSOLIDER 101 and ADSOLIDER 102) manufactured by Freund Inc., and AEROSIL Series (e.g., AEROSIL 200 and AEROSIL 300) manufactured by Nippon Aerosil Co., Ltd. Moreover, the second spherical porous carrier may be used. Such a second spherical porous carrier is, for example, available as trade name numbers "H-51", "H-52", and "H-53" of "SUN-SPHERE" (manufactured by Asahi Glass Co., Ltd.). Use of the second spherical porous carrier can improve handleability and workability of a preparation process including a tablet compression (or tableting) step due to a high flowability and a small bulk density thereof.

The second porous carrier may contain much more hydroxyl groups (or silanol groups) compared with the first porous carrier. The heating loss (ignition loss) of the second porous carrier may be, for example, not less than 4.5% by weight (e.g., about 5 to 17% by weight) and particularly about 5 to 15% by weight (e.g., about 7 to 10% by weight) at a temperature of 950° C. for 2 hours. The porous silicon-containing carrier as the second porous carrier may have the following intensity ratios in an infrared absorption spectrum.

(1) Intensity Ratio Relative to the Absorption Intensity $I_0$ (1-11) Intensity ratio ($I_1/I_0$): about 2.5 to 15 (e.g., about 5 to 12, particularly about 6 to 12), preferably about 7 to 10 (e.g., about 7.3 to 9.5), and more preferably about 7.5 to 9 (e.g., about 7.5 to 8.5)

(1-12) Intensity ratio ($I_2/I_0$): about 5 to 30 (e.g., about 7 to 28, particularly about 10 to 27), preferably about 15 to 25 (e.g., about 19 to 23), and more preferably about 19.5 to 22.5

The intensity ratio ($I_2/I_0$) may be as follows. Intensity ratio ($I_2/I_0$): about 5 to 15 (e.g., about 6 to 12), and preferably about 7 to 10 (e.g., about 7.5 to 9.5)

(1-13) Intensity ratio ($I_3/I_0$): about 10 to 65 (e.g., about 20 to 60), preferably about 35 to 55 (e.g., about 40 to 50), and more preferably about 44 to 48

(1-14) Intensity ratio ($I_4/I_0$): about 13 to 120 (e.g., about 20 to 115), preferably about 65 to 110 (e.g., about 70 to 100), and more preferably about 75 to 95 (e.g., about 80 to 90)

The intensity ratio ($I_4/I_0$) may be as follows. ($I_4/I_0$): about 13 to 30 (e.g., about 15 to 28), preferably about 17 to 27 (e.g., about 18 to 25), and more preferably about 20 to 23

(1-15) Intensity ratio ($I_5/I_0$): about 25 to 150 (e.g., about 50 to 145), preferably about 75 to 140 (e.g., about 100 to 135), and more preferably about 110 to 130

(1-16) Intensity ratio ($I_6/I_0$): about 15 to 125 (e.g., about 30 to 120), preferably about 50 to 115 (e.g., about 75 to 110), and more preferably about 95 to 110

The intensity ratio ($I_6/I_0$) may be as follows. Intensity ratio ($I_6/I_0$): about 15 to 40 (e.g., about 17 to 37), preferably about 20 to 35 (e.g., about 23 to 33), and more preferably about 25 to 33

(1-17) Intensity ratio ($I_7/I_0$): about 10 to 75 (e.g., about 20 to 70), preferably about 30 to 65 (e.g., about 45 to 60), and more preferably about 50 to 60

(1-18) Intensity ratio ($I_8/I_0$): about 8 to 65 (e.g., about 15 to 60), preferably about 25 to 50 (e.g., about 28 to 45), and more preferably about 30 to 35

The intensity ratio ($I_8/I_0$) may be as follows. Intensity ratio ($I_8/I_0$): about 8 to 20 (e.g., about 10 to 18), preferably about 12 to 18 (e.g., about 13 to 17), more preferably about 13.5 to 16.5 (e.g., about 14.5 to 16.5)

(1-19) Intensity ratio ($I_9/I_0$): about 3 to 20 (e.g., about 10 to 18), preferably about 12 to 17 (e.g., about 12.5 to 16), and more preferably about 13 to 15

The intensity ratio ($I_9/I_0$) may be as follows. Intensity ratio ($I_9/I_0$): about 3 to 15 (e.g., about 5 to 13), preferably about 6 to 12, and more preferably about 7 to 11 (e.g., about 8 to 10)

(1-20) Intensity ratio ($I_{10}/I_0$): about 1 to 10 (e.g., about 2 to 8), preferably about 3 to 7 (e.g., about 3.5 to 6.5), and more preferably about 4.7 to 6 (e.g., about 4.8 to 5.7)

The intensity ratio ($I_{10}/I_0$) may be as follows. Intensity ratio ($I_{10}/I_0$): preferably about 2.5 to 6.5 (e.g., about 3 to 6), more preferably about 3.5 to 5.5 (e.g., about 3.5 to 5), and particularly about 3.7 to 4.7

(2) Intensity Ratio Relative to the Absorption Intensity $I_1$ (2-11) Intensity ratio ($I_3/I_1$): about 4 to 10 (e.g., about 4.5 to 10), preferably about 5 to 8 (e.g., about 5.5 to 7.5), and more preferably 5.7 to 7 (e.g., about 5.8 to 6.5)

(2-12) Intensity ratio ($I_4/I_1$): about 7 to 15, preferably about 8 to 13 (e.g., about 10 to 13), and more preferably about 10.5 to 12.5 (e.g., about 10.5 to 12)

(2-13) Intensity ratio ($I_5/I_1$): about 10 to 20, preferably about 12 to 19 (e.g., about 13 to 18), and more preferably about 14 to 17 (e.g., about 15 to 16.5)

(2-14) Intensity ratio ($I_6/I_1$): about 8 to 18, preferably about 10 to 16 (e.g., about 11 to 15.5), and more preferably about 12 to 15 (e.g., about 12.5 to 14.5)

(2-15) Intensity ratio ($I_7/I_1$): about 5 to 12, preferably about 5.5 to 10 (e.g., about 5.5 to 8.5), and more preferably about 6 to 8 (e.g., about 6.5 to 7.7)

(2-16) Intensity ratio ($I_8/I_1$): about 3.2 to 8, preferably about 3.5 to 6 (e.g., about 3.5 to 6), and more preferably about 3.7 to 5 (e.g., about 3.8 to 4.8)

Incidentally, these porous silicon-containing carriers also may satisfy at least one of the above-mentioned intensity ratios and may satisfy a plurality of the above-mentioned intensity ratios (e.g., two intensity ratios such as the intensity ratio ($I_2/I_0$) and the intensity ratio ($I_3/I_0$)) or all of the above-mentioned intensity ratios.

The mean particle size of the second porous carrier is not particularly limited to a specific one, and may be selected, for example, from the range of about 1 to 20 μm, and may be about 2 to 15 μm, preferably about 3 to 10 μm, and particularly about 4 to 10 μm (e.g., about 4 to 8 μm).

The second porous carrier also has a large number of pores. The mean pore size of the second porous carrier may be, for example, about 1 to 30 nm, preferably about 2 to 27 nm (e.g., about 3 to 25 nm), and more preferably about 5 to 22 nm (e.g., about 6 to 20 nm). Moreover, the mean pore volume of the second porous carrier may be, for example, about 0.1 to 5 mL/g, preferably about 0.3 to 3 mL/g, more preferably about 0.5 to 2 mL/g (e.g., about 0.7 to 1.75 mL/g), and particularly about 1 to 1.7 mL/g. The specific surface area of the second porous carrier is not particularly limited to a specific one, and may be, for example, about 100 to 1000 $m^2/g$ (e.g., about 200 to 800 $m^2/g$) and preferably about 250 to 750 $m^2/g$ (e.g., about 300 to 700 $m^2/g$).

The oil absorption (or oil absorption amount) of the second porous carrier (unit: ml/100 g) may be, for example, about 75 to 500 (preferably about 90 to 400, more preferably about 100 to 350, and particularly about 150 to 350 (e.g., about 170 to 320)). The sedimentation volume of the second porous carrier measured by the stationary method (apparent specific gravity, unit: ml/5 g) may be, for example, about 10 to 120 (preferably about 20 to 110, and more preferably about 30 to 100).

The porous silicon-containing carrier as the second porous carrier may have a silanol group like the first porous carrier. In order to reduce or adjust the silanol group concentration, the porous silicon-containing carrier may be surface-treated with the above-mentioned surface-treating agent like the first porous carrier.

The proportion of the first porous carrier (e.g., a spherical porous carrier) relative to the second porous carrier (e.g., an amorphous porous carrier) may be selected from the range in which the solubility of the active ingredient is not deteriorated, and the proportion [the former/the latter (weight ratio)] is usually about 50/50 to 100/0 (e.g., about 55/45 to 99/1), preferably about 60/40 to 100/0 (e.g., about 65/35 to 95/5), more preferably about 70/30 to 100/0 (e.g., about 75/25 to 90/10), and particularly about 75/25 to 100/0. Increase of proportion of the second porous carrier tends to reduce the solubility of the active ingredient.

The amount of the active ingredient supported on or to the powdery porous carrier may be selected from the range of about 0.01 to 10 parts by weight (for example, about 0.01 to 5 parts by weight) of the active ingredient relative to 1 part by weight of the powdery porous carrier depending on the species of the carrier or active ingredient, or others. For example, the amount of the active ingredient may be about 0.1 to 5 parts by weight (e.g., about 0.2 to 4 parts by weight), preferably about 0.25 to 3 parts by weight (e.g., about 0.3 to 2.5 parts by weight), more preferably about 0.5 to 2 parts by weight (e.g., about 0.5 to 1.5 parts by weight), and particularly about 0.7 to 1.2 parts by weight, relative to 1 part by weight of the powdery porous carrier. The present invention improves the solubility of the active ingredient and the bioavailability remarkably. Therefore, the present invention realizes a higher bioavailability while the amount of the active ingredient is reduced. For example, in the solid dispersion of the present invention, even when the amount of the active ingredient reduces about 10 to 50% by weight, preferably about 20 to 45% by weight (e.g., about 25 to 35% by weight) comparing with the conventional amount of the active ingredient, the bioavailability compatible with the conventional bioavailability can be obtained. Moreover, since the powdery porous carrier functions as an excipient, the solid dispersion also has a high compression moldability. Therefore, the solid dispersion realizes a compact or small size preparation, thereby improving the easiness of dosing and patient compliance.

The solid dispersion may contain not only the above-mentioned active ingredient but also various pharmaceutically acceptable components (or additive components, carrier components), for example, an excipient, a binder, and a disintegrant. Among these additive components, in order to control the wettability between the porous carrier and the active ingredient and the impregnating performance and solubility of the active ingredient, it is preferred to use at least one member selected from the group consisting of a water-soluble polymer, an excipient, and a surfactant. In order to control the solubility of the active ingredient, a lipid may be used. In particular, in order to control the impregnating performance of the active ingredient to the porous carrier, the impregnation operability, the solubility of the active ingredient, and others, the solid dispersion may further contain at least one component selected from a water-soluble polymer, a saccharide, a surfactant, a lipid, and others. These components may be supported on the carrier together with the active ingredient or may be supported on a carrier other than the carrier of the solid dispersion. The additive component is practically a water-soluble component (particularly, at least one water-soluble component selected from the group consisting of a water-soluble polymer, a saccharide, and a surfactant). Incidentally, the additive component (particularly, a water-soluble additive component) may have a low affinity or compatibility to the hardly water-soluble active ingredient (or hydrophobic active ingredient) and may be a component which cannot dissolve or disperse the active ingredient in the form of molecule or fine particle (or may be an additive component which cannot form a meltable solid dispersion containing the active ingredient dissolved or dispersed at a molecule level or fine particle level and does not serve as a solid matrix of the solid dispersion).

The water-soluble polymer may include, for example, a soluble starch; a polysaccharide such as gum acacia (or gum arabic), dextrin, sodium alginate, a hyaluronic acid, or a sodium chondroitin sulfate; a homo- or copolymer of vinylpyrrolidone such as a polyvinylpyrrolidone (povidone)

or a vinylpyrrolidone-vinyl acetate copolymer (copovidone); a polyvinyl alcohol; a carboxyvinyl polymer (e.g., CARBOPOL 934, 940, and a carbomer); a homo- or copolymer of (meth)acrylic acid, such as a polyacrylic acid-series polymer or a polymethacrylic acid-series polymer (e.g., eudragit L, LD, and S); a synthetic polymer such as a polyethylene glycol (e.g., a macrogol); and a cellulose ether such as a methyl cellulose, a carboxymethyl cellulose, a carboxymethyl cellulose sodium, a carboxymethyl cellulose potassium, a hydroxyethyl cellulose (HEC), a hydroxyethyl methyl cellulose, a hydroxypropyl cellulose (HPC), or a hydroxypropyl methyl cellulose (HPMC). These water-soluble polymers may be used singly or in combination. Among these water-soluble polymers, the preferred one is a homo- or copolymer of vinylpyrrolidone (such as a polyvinylpyrrolidone (povidone)), a carboxyvinyl polymer, a homo- or copolymer of acrylic acid (such as a polyacrylic acid-series polymer), a polyethylene glycol (e.g., a macrogol), a cellulose ether (such as an HPMC or an HPC), or others. In particular, a polyvinylpyrrolidone (povidone), a carboxyvinyl polymer, a polyethylene glycol (e.g., macrogol), an HPMC, an HPC, and others are preferred. The HPMC includes HPMC 2208, HPMC 2906, HPMC 910, and others. The HPC includes an HPC containing about 53 to 78% of hydroxypropoxy group. At least one water-soluble cellulose ether selected from the group consisting of the HPMC and the HPC is practically used as the water-soluble polymer.

The saccharide may include, for example, a saccharide (a monosaccharide, or an oligosaccharide such as a disaccharide) or a sugar alcohol such as lactose, white soft sugar or refined sugar, glucose, fructose, sucrose, maltose, hydrogenated maltose, multitol, mannitol, sorbitol, or xylitol. These saccharides may be used singly or in combination. Among these saccharides, the sugar alcohol (e.g., mannitol) is preferred.

The surfactant may include an anionic surfactant (e.g., a sulfonic acid or a salt thereof such as benzenesulfonic acid, dodecylbenzenesulfonic acid, or dodecanesulfonic acid; an alkyl sulfate such as sodium dodecyl sulfate or sodium lauryl sulfate (SLS) (e.g., an alkali metal salt of a $C_{6-30}$alkylsulfonic acid); a salt of a sulfoaliphatic dicarboxylic acid ester (e.g., a sulfosuccinate such as disodium lauryl sulfosuccinate); a metal salt of a long-chain (or highly) fatty acid such as calcium stearate; bile acid or a salt thereof; and a cholic acid compound such as cholic acid or deoxycholic acid), a cationic surfactant (e.g., a tetraalkylammonium salt such as a tetraalkylammonium halide; benzethonium chloride, benzalkonium chloride, and cetylpyridinium chloride), a nonionic surfactant (e.g., a sucrose ester of a long-chain fatty acid such as sucrose palmitate, sucrose stearate, or sucrose oleate; a (poly)ethylene glycol long-chain fatty acid ester such as ethylene glycol mono- or distearate, a polyethylene glycol mono- or dioleate, a polyethylene glycol mono- or distearate, or a polyoxyethylene-hardened castor oil; a (poly)glycerin long-chain fatty acid ester such as decaglycerin monocaprylate, glycerin monocaprylate monostearate, or glycerin monooleate; a sorbitan long-chain fatty acid ester such as sorbitan monolaurate, sorbitan mono- to tristearate, or sorbitan mono- to trioleate; a sorbit long-chain fatty acid ester corresponding to the sorbitan long-chain fatty acid ester; a (poly)oxyethylene sorbitan long-chain fatty acid ester such as a polyoxyethylene sorbitan monolaurate (e.g., a polysorbate), a polyoxyethylene sorbitan monostearate, a polyoxyethylene sorbitan monooleate, or a polyoxyethylene sorbitan monopalm oil long-chain fatty acid ester; a (poly)oxyethylene sorbit long-chain fatty acid ester corresponding to the polyoxyethylene sorbitan long-chain fatty acid ester; a polyoxyalkylene long-chain fatty acid amide such as a polyoxyethylene stearamide; a polyoxyethylene higher alcohol ether such as a polyoxyethylene lauryl ether, a polyoxyethylene stearyl ether, or a polyoxyethylene oleyl ether; and a polyoxyethylene polyoxypropylene glycol), an amphoteric surfactant (e.g., a glycin compound such as dodecyl-di-(aminoethyl)glycin; a betaine compound such as betaine or dimethyldodecylcarboxybetaine; and a phosphatidic acid derivative such as lecithin), and a polymeric surfactant (e.g., a polyoxyethylene polyoxypropylene glycol such as Pluronic or Poloxamer; a polyethylene oxide-(meth)acrylate copolymer; a polyethylene oxide-epichlorohydrin copolymer; a polyether ester amide, a polyether amide imide, and a polyether ester). Incidentally, the above-mentioned long-chain fatty acid may include a $C_{8-26}$ saturated or unsaturated fatty acid, and preferably a $C_{12-20}$ saturated or unsaturated fatty acid. These surfactants may be used singly or in combination.

Among these surfactants, the preferred one is an anionic surfactant [e.g., a sodium $C_{10-24}$alkyl sulfate such as SLS, and sulfosuccinate] and/or a nonionic surfactant [e.g., a sucrose $C_{8-26}$fatty acid ester, a (poly)glycerin $C_{8-26}$fatty acid ester, a sorbitan $C_{8-26}$fatty acid ester, and a (poly) oxyethylene sorbitan long-chain fatty acid ester such as a polysorbate], a polyoxyethylene polyoxypropylene glycol such as Pluronic or Poloxamer, and others. Incidentally, a polyoxyethylene polyoxypropylene glycol as the polymeric surfactant can be classified as the nonionic surfactant.

The lipid may include a wax (e.g., a bees wax, a carnauba wax, a cacao butter (or a cacao oil), a lanolin, a paraffin, and a petrolatum), a long-chain fatty acid ester (e.g., a saturated or unsaturated fatty acid alkyl ester, an ester of a fatty acid with a polyhydric alcohol (such as a poly$C_{2-4}$alkylene glycol, glycerin, or a polyglycerin) (e.g., a fat and oil, e.g., a glyceride, and a hardened (or hydrogenated) oil such as a hardened castor oil), a phospholipid, a higher alcohol (e.g., a saturated or unsaturated higher alcohol such as stearyl alcohol or oleyl alcohol), a higher fatty acid (a saturated or unsaturated higher fatty acid such as oleic acid, linoleic acid, linolenic acid, or stearic acid), a metallic soap (e.g., a metal salt of a fatty acid such as a sodium salt of a palm oil fatty acid, or calcium stearate), and others. These lipids may be used singly or in combination.

Incidentally, among these components, in order to improve the uniformity of the solid dispersion, it is advantageous to use at least the water-soluble polymer and/or the surfactant.

The supported amounts or amounts to be used of these components may be selected depending on the properties of the solid dispersion, and the amount of each of these components may usually be selected from the range of about 0.1 to 100 parts by weight (e.g., about 1 to 50 parts by weight), preferably about 0.5 to 50 parts by weight, and more preferably about 1.5 to 30 parts by weight (e.g., about 2.5 to 25 parts by weight) relative to 100 parts by weight of the active ingredient. The amount of each component may usually be about 1.5 to 20 parts by weight (e.g., about 1.5 to 15 parts by weight) relative to 100 parts by weight of the active ingredient. Moreover, the amount of each additive component may be selected from the range of about 3 to 50 parts by weight and preferably about 5 to 30 parts by weight (e.g., about 7 to 25 parts by weight) relative to 100 parts by weight of the active ingredient. The amount of each additive component may usually be about 5 to 20 parts by weight (e.g., about 5 to 15 parts by weight).

Incidentally, according to the present invention, it is unnecessary to heat and melt-mix the additive component and the active ingredient for preparing a solid dispersion (a meltable dispersion (solid dispersion) having the active ingredient in the form of a molecule or fine particle contained in the additive component as a vehicle or solid matrix). Further, the powdery porous carrier comprising the first porous carrier serves as an excipient for a solid preparation, and the additive component improves the wettability and impregnating performance of the active ingredient to the powdery porous carrier. Furthermore, the powdery porous carrier can improve the solubility (or dissolution rate) and bioavailability of the active ingredient. Therefore, the amount of the additive component can be greatly reduced, and the dosage form can be reduced in size. A compression molding of a solid dispersion containing a light anhydrous silic acid significantly deteriorates the solubility (or dissolution rate) of the active ingredient from the obtained molded product (sized granules or tablets). Therefore, in order to improve the solubility (or dissolution rate), the compression molding requires to add a large amount of a disintegrant. On the other hand, the present invention realizes a high solubility (or dissolution rate) even in a small amount of a disintegrant.

The proportion of each additive component (for example, a component selected from the group consisting of a water-soluble polymer, a saccharide, and a surfactant) to be supported on the porous carrier may be, for example, about 0.1 to 30 parts by weight (e.g., about 0.5 to 25 parts by weight), preferably about 1 to 20 parts by weight (e.g., about 1.5 to 20 parts by weight), and more preferably about 2 to 15 parts by weight (e.g., about 2.5 to 13 parts by weight) relative to 100 parts by weight of the hardly water-soluble active ingredient. Moreover, the amount of each additive component may be about 1 to 30 parts by weight (e.g., about 2 to 25 parts by weight), preferably about 3 to 20 parts by weight (e.g., about 5 to 20 parts by weight), and more preferably about 5 to 15 parts by weight (e.g., about 7 to 13 parts by weight) relative to 100 parts by weight of the active ingredient. Further, the total amount of the additive component (e.g., the water-soluble cellulose ether and the surfactant) may be, for example, selected from the range of about 1 to 100 parts by weight relative to 100 parts by weight of the hardly water-soluble active ingredient (e.g., a fenofibrate component). The total amount may usually be about 1 to 50 parts by weight (e.g., about 3 to 50 parts by weight), preferably about 5 to 40 parts by weight (e.g., about 5 to 30 parts by weight), more preferably about 10 to 40 parts by weight (e.g., about 10 to 30 parts by weight), and particularly about 10 to 25 parts by weight.

Process for Producing Solid Dispersion

According to the present invention, a solid dispersion containing the powdery porous carrier and the active ingredient supported on or to the carrier can be produced without treating with a supercritical fluid (e.g., a supercritical water) or a subcritical fluid (e.g., a subcritical water). Specifically, the solid dispersion containing the porous carrier and the active ingredient supported on or to the carrier can be produced by impregnating a powdery porous carrier comprising at least the first porous carrier with a solution containing an organic solvent and the above-mentioned hardly soluble active ingredient, and removing the organic solvent from the mixture. According to the present invention, it is unnecessary to prepare a meltable dispersion (solid dispersion) having the active ingredient dissolved or finely dispersed in the matrix component by heat-melting the matrix component and the active ingredient and spray the molten solid dispersion on the carrier. Therefore, since the active ingredient is not thermally deteriorated, the present invention is applicable to a wide range of active ingredients and can improve the solubility (or dissolution rate) and bioavailability of the active ingredient easily and efficiently.

The organic solvent is not particularly limited to a specific one as long as the hardly soluble active ingredient (and a component such as the above-mentioned water-soluble polymer) is soluble in the solvent. The organic solvent may include, for example, an alcohol (e.g., methanol, ethanol, propanol, isopropanol, and butanol), an ester (e.g., ethyl acetate and butyl acetate), a ketone (e.g., acetone, ethyl methyl ketone, and methyl isobutyl ketone), an ether (e.g., a chain ether such as ethyl ether or propyl ether, and a cyclic ether such as dioxane or tetrahydrofuran), a cellosolve (e.g., ethyl cellosolve), a cellosolve acetate, a carbitol (e.g., methylcarbitol), a hydrocarbon (e.g., an aliphatic hydrocarbon such as hexane, an alicyclic hydrocarbon such as cyclohexane, and an aromatic hydrocarbon such as toluene), a halogenated hydrocarbon (e.g., methylene chloride), dimethylsulfoxide, N-methylpyrrolidone, a nitrile, and an amide. These organic solvents may be used singly or in combination. Incidentally, if necessary, water may be used in combination with the organic solvent as long as the active ingredient can be dissolved in the solvent. Ethanol, isopropanol, acetone, or others is practically employed as the organic solvent.

The concentration of the active ingredient in the solution containing the organic solvent may be about 1 to 50 wt/vol %, preferably about 5 to 30 wt/vol % (e.g., about 10 to 25 wt/vol %), and more preferably about 7 to 20 wt/vol % (e.g., about 10 to 15 wt/vol %) in terms of a solid content. Moreover, the solution containing the hardly soluble active ingredient and the organic solvent is usually in a liquid form at a room temperature (a temperature of 15 to 25° C.), preferably a temperature of 10° C., more preferably a temperature of 5° C., and particularly a temperature of 0° C.

According to the present invention, since the porous carrier is impregnated with the solution containing the active ingredient and the additive component and the organic solvent, the active ingredient and the additive component can uniformly permeate (or penetrate) the porous carrier to a deep region without being disproportionately supported on the surface of the porous carrier, and can be uniformly supported throughout the porous carrier. Use of the solution containing the additive component (for example, at least one component selected from the group consisting of a water-soluble polymer, a saccharide, and a surfactant) and the organic solvent can improve the permeation (or penetration) property or impregnating performance of the hardly soluble active ingredient to the porous carrier.

In the impregnation step, it is sufficient to bring the solution containing the organic solvent and the hardly soluble active ingredient into contact with the powdery porous carrier. The solution may be applied to the porous carrier by spraying or the like. In practical cases, the porous carrier is allowed to stand in the solution in a stirring or stationary condition for impregnation, or the solution and the porous carrier are mixed together for impregnation. The powdery porous carrier is practically impregnated with the solution containing the organic solvent at a room temperature by immersing the powdery porous carrier in the solution. By the contact of the active ingredient with the carrier, the active ingredient in the organic solvent enters into the pores of the porous carrier and is supported on or to the porous carrier. Incidentally, most of the active ingredient seems to enter the pores of the porous carrier or to be adsorbed into the pores of the porous carrier.

The impregnating operation is usually carried out under an atmospheric pressure. If necessary, the operation may be carried out under a reduced pressure or an applied pressure.

Moreover, the impregnating operation can be carried out at a temperature below a boiling point of the organic solvent and is usually carried out at a temperature of about 0 to 50° C., preferably about 5 to 35° C. (e.g., about 10 to 30° C.), and more preferably about 15 to 25° C. The impregnating operation can be carried out at a room temperature (e.g., about 10 to 35° C., preferably about 15 to 30° C., and particularly about 15 to 25° C.). The impregnating operation may optionally be conducted under warming or heating. Further, if necessary, the porous carrier impregnated with the active ingredient may be separated by a method such as a filtration or a centrifugation and washed.

By drying the mixture (the mixture containing the powdery porous carrier impregnated with the active ingredient) to remove the organic solvent, a solid dispersion is obtained. That is, the residual organic solvent can be removed from the powdery porous carrier to give a dispersion (solid dispersion) having the active ingredient dispersed in the porous carrier. The active ingredient is usually dispersed and supported on the porous carrier uniformly. According to the present invention, since the porous carrier is impregnated with the solution containing the organic solvent without spraying a molten solid dispersion containing the meltable matrix and the active ingredient on the porous carrier, the active ingredient and the additive component are usually supported throughout the porous carrier. The removal of the organic solvent may be conducted by a conventional method, for example, a drying method (air drying, heat drying). The drying may be carried out under an atmosphere pressure or a reduced pressure.

Incidentally, when the solvent is removed by lyophilizing or spray-drying a mixture of the powdery porous carrier and the solution containing the active ingredient and the organic solvent, the solid dispersion can be produced efficiently. In particular, the spray drying of the mixture of the powdery porous carrier and the solution containing the active ingredient and the organic solvent produces a uniform or homogeneous solid dispersion efficiently. The lyophilization or spray drying may be performed by a conventional technique. For example, the spray drying may be carried out by spraying the mixture in an atmospheric (or air) stream to dry the mixture by a warm current (or air) and/or a hot current (or air).

The solid dispersion of the present invention is not particularly limited to a specific one as long as the solid dispersion contains the porous carrier and the active ingredient supported on or to the carrier with impregnation; and the solid dispersion may be a mixture of the active ingredient and the porous carrier. The active ingredient is usually dispersed in and supported on or to the porous carrier uniformly. In particular, since the active ingredient is dispersed in the state that the active ingredient is incorporated in the pores of the porous carrier, the solubility (or dissolution rate) of the active ingredient can be remarkably improved. Accordingly, even when the amount of the active ingredient is reduced, the bioavailability of the ingredient can be improved.

The solid dispersion of the present invention alone may be used as a pharmaceutical. Since the solid dispersion has an excellent compression moldability, the solid dispersion may be subjected to a compression molding, crushing, and sizing to give granules, or may be compressed to produce tablets. The solid dispersion of the present invention is practically used as a pharmaceutical composition (such as a solid preparation) in combination with a pharmaceutically acceptable carrier or additive (e.g., the above-exemplified carrier or additive).

Pharmaceutical Composition and Process for Producing Pharmaceutical Composition

The pharmaceutical composition of the present invention is not particularly limited to a specific one as long as the composition contains the solid dispersion containing the powdery porous carrier comprising the first porous carrier and the hardly water-soluble active ingredient supported on the powdery porous carrier. The pharmaceutical composition may contain a plurality of active ingredients. At least one active ingredient of the plurality of active ingredients is hardly (or sparingly) soluble in water. These active ingredients may comprise a plurality of active ingredients hardly soluble in water or may contain a water-soluble active ingredient. Moreover, all of these active ingredients may be supported on a single porous carrier (the first porous carrier), or these active ingredients may be independently supported on a plurality of powdery porous carriers (a plurality of porous carriers comprising at least the first porous carrier). In the latter case, it is not essentially necessary that all of these porous carriers be the above-mentioned specific powdery porous carrier used in the present invention. Moreover, all or part of the active ingredients may be supported on the powdery porous carrier. The pharmaceutical composition may contain other active ingredient(s), which is(are) not supported on the porous carrier, in various forms.

Further, regarding the pharmaceutical composition containing the higher-dose active ingredient and the lower-dose active ingredient, the lower-dose active ingredient (e.g., the hardly water-soluble active ingredient) may be supported on the porous carrier. It is preferable that at least the higher-dose active ingredient be supported on the porous carrier (the powdery porous carrier comprising at least the first porous carrier, particularly the first porous carrier). In particular, it is preferable that a hardly water-soluble active ingredient to be administered with a higher dose be supported on the porous carrier (the powdery porous carrier comprising at least the first porous carrier, particularly the first porous carrier). For example, when a hardly water-soluble active ingredient to be administered with a higher dose and a hardly water-soluble active ingredient to be administered with a lower dose are used in combination, it is preferable that at least the active ingredient to be administered with a higher dose be supported on the first porous carrier. More specifically, a pharmaceutical composition containing, for example, a fibrate compound (e.g., fenofibrate) and a statin-series compound (e.g., pitavastatin or pitavastatin calcium) among hypolipidemic agents, preferably comprises a solid dispersion having at least the fibrate compound supported on the powdery porous carrier. In the preparation, the statin-series compound may be supported on the porous carrier, or the pharmaceutical composition may contain the statin-series compound in a form isolated from the solid dispersion (in a form such as a mixture or a preparation).

Incidentally, with respect to a preparation which contains a solid dispersion having a porous carrier (particularly, the first porous carrier) and a higher-dose active ingredient supported on the porous carrier, and a lower-dose active ingredient (particularly, an active ingredient which is not supported on the porous carrier), the lower-dose active ingredient can be added in various steps for producing the pharmaceutical composition. For example, when tablets are produced by a tablet compression after preparing granules containing the solid dispersion, the lower-dose active ingredient may be added in the process of the granulation or added to the resulting granules before the tablet compression.

The lower-dose active ingredient may include an angina-treating agent, a hypertension-treating agent, a hypotension-treating agent, an antiobesity agent, an agent for treating heart failure, an agent for treating myocardial infarction, an antiarrhythmic agent, a diabetic agent, an agent for treating diabetic complication, an agent for treating peptic ulcer, a febrifuge, an analgesic, an antiphlogistic, a stomachic, a digestant, an antacid, an antiemetic, an antitussive expectorant, an agent for treating bronchial asthma, a constipation-treating agent, a diarrhea-treating agent (or an antidiarreheal), an agent for treating hepatic disease, an agent for treating biliary tract and spleen system, a hemorrhoid-treating agent, an agent for treating thyroid disease, a hyperlithuria-treating agent, a rheumatism-treating agent (or an antirheumatic), an antibiotic, an antidepressant, an antiallergic agent, an antituberculous agent, a prostatomegaly-treating agent, an osteoporosis-treating agent, an agent for treating Alzheimer's disease, and others.

The hypolipidemic agent may include an HMG-CoA reductase inhibitor, for example, a statin-series compound such as simvastatin, lovastatin, atorvastatin, pitavastatin, rosuvastatin, cerivastatin, itavastatin, pravastatin, fluvastatin, or a salt thereof (e.g., a sodium salt and a calcium salt), and small intestine cholesterol transporter inhibitor (e.g., ezetimibe).

The hypertension-treating agent may include, for example, an angiotensin converting enzyme inhibitor (e.g., captopril, enalapril, delapril, imidapril, quinapril, temocapril, cilazapril, trandolapril, lisinopril, or a salt thereof), an angiotensin II antagonist (e.g., candesartan cilexetil, losartan, valsartan, telmisartan, olmesartan medoxomil, or a salt thereof), a calcium antagonist (e.g., manidipine, nifedipine, nicardipine, amlodipine, efonidipine, or a salt thereof), clonidine hydrochloride, and bunazosin hydrochloride.

The antiobesity agent may include, for example, a central antiobesity agent (e.g., mazindol).

The agent for treating heart failure may include, for example, a thiazide-series compound (e.g., trichlormethiazide and hydrochlorothiazide), a non-thiazide-series compound (e.g., tripamide), an aldosterone antagonist-series compound (e.g., spironolactone), a chlorobenzenesulfonamide-series compound (e.g., mefruside and indapamide), azosemide, isosorbide nitrate, piretanide, and bumetanide.

The agent for treating myocardial infarction may include, for example, a warfarin (e.g., warfarin potassium), an antithrombin agent (e.g., aragatroban), and a platelet aggregate inhibitor (e.g., ethyl icosapentate, beraprost sodium, aspirin, and clipidogrel sulfate).

The diabetic agent may include, for example, an insulin preparation, an $\alpha$-glucosidase inhibitor (e.g., voglibose and miglitol), an insulin secretagogue (e.g., tolbutamide, glibenglamide, gliclazide, and glimepiride), and an insulin resistance improving agent (e.g., pioglitazone hydrochloride).

The agent for treating diabetic complication may include, for example, an active oxygen scavenger (e.g., thioctic acid), and a carebral vasodilator (e.g., tiapride).

The agent for treating peptic ulcer may include, for example, a proton pump inhibitor (e.g., omeprazole and lansoprazole), and a defensive factor enhancing agent (e.g., metoclopramide).

The rheumatism-treating agent may include, for example, an immunosuppressant (e.g., leflunomide and methotrexate), and auranofin.

The antiallergic agent may include, for example, an antihistamine (e.g., clemastine fumarate, loratadine, mequitazine, ebastine, oxatomide, and bepotastine besilate).

Further, when the pharmaceutical composition contains a plurality of active ingredients, the form (or shape) of the pharmaceutical composition may be, for example, either a single preparation or a kit preparation. For example, the pharmaceutical composition containing, for example, a fibrate compound (e.g., fenofibrate) and a statin-series compound (e.g., pitavastatin) among hypolipidemic agents may be in the form that at least the fibrate compound is supported on the powdery porous carrier, for example, (a) a single pharmaceutical composition (preparation) containing the statin-series compound and a solid dispersion having the fibrate compound supported on the powdery porous carrier, (b) a pharmaceutical composition (preparation) containing a solid dispersion having both the fibrate compound and the statin-series compound supported on the powdery porous carrier, and (c) a pharmaceutical composition in a kit form (kit preparation) which comprises a preparation containing a solid dispersion having the fibrate compound supported on the powdery porous carrier and a preparation containing the statin-series compound.

In the pharmaceutical composition, the dosage form is not particularly limited to a specific one and may be a semisolid preparation (for example, creams, jellys, gumdrop-like preparations, ointments, and gels), a liquid preparation (for example, suspensions, emulsions, and syrup). The dosage form is usually a solid preparation (for example, powdered preparations, powders, granulated preparations (granules, fine (or microfine) granules, or the like), spherical or spheroidal preparations, pills, tablets (including sublingual tablets, orally disintegrating tablets, troches, chewable tablets, and others), capsules (including hard capsules, soft capsules, and microcapsules), dry syrups, suppositories, film-like preparations, and sheet-like preparations) in practical cases. Incidentally, the capsules may be a capsule filled with a liquid (e.g., a soft capsule) or a capsule filled with a solid preparation (such as solid dispersion or granules). Moreover, the powdered preparations and/or liquid preparations may be used in the form of injections, sprays or aerosols. Further, the preparation may be an oral dosage form or a parenteral dosage form (for example, ophthalmic solutions, collunariums, inhalants, and plasters and pressure sensitive adhesives (such as cataplasms)). Further, the preparation may be topical or local administration form (e.g., suppositories). If necessary, the pharmaceutical composition of the present invention may be a rapid-release preparation or a sustained release preparation. The preparation of the present invention is usually a solid preparation for oral administration, for example, powders, tablets (e.g., uncoated tablets), granules, spherical or spheroidal preparations, capsules, and film-like preparations, preferably tablets, granules, and capsules.

The carrier may be selected, depending on the form (dosage form), the administration route, the application, and others of the pharmaceutical composition (or preparation), from various components (e.g., an excipient, a binder, a disintegrant, a lubricant, and a coating agent) listed in Japanese Pharmacopoeia, and another publications such as (1) Handbook of Pharmaceutical Excipients (Maruzen Company, ltd., (1989)), (2) Japanese Pharmaceutical Excipients Dictionary 2000 (Yakuji Nippo Ltd., issued March, 2002), (3) Japanese Pharmaceutical Excipients Dictionary 2005) (Yakuji Nippo Ltd., issued May, 2005), (4) Pharmaceutics, revised fifth edition (Nankodo, Co., Ltd. (1997)), and (5) Japanese Pharmaceutical Excipients 2003 (Yakuji Nippo Ltd., issued August, 2003). The carrier or additive for the pharmaceutical composition (particularly, the solid preparation) is practically at least one member selected from the group consisting of an excipient, a binder, and a disintegrant. An additive such as a lipid may be used.

In particular, the solid dispersion of the present invention does not deteriorate the solubility (or dissolution rate) of the active ingredient even by compression molding. More specifically, for example, when a solid dispersion prepared by using a light anhydrous silic acid (e.g., "SYLYSIA 350") is compression-molded into a molded product (sized granules or tablets), the molded product remarkably deteriorates the solubility of the active ingredient. On the other hand, a compression-molded product of the solid dispersion of the present invention can remarkably improve the solubility of the active ingredient. Therefore, the present invention is advantageously applied to a pharmaceutical composition containing a component ordinarily subjected to a compression molding step, for example, at least one carrier or additive component selected from the group consisting of an excipient, a binder, a disintegrant, and a lubricant. That is, the present invention is advantageously applied to a solid preparation in which the solid dispersion is compression-molded.

The excipient may include a saccharide or a sugar alcohol such as lactose, white sugar or refined sugar, glucose, sucrose, mannitol, sorbitol, or xylitol; a starch such as a corn starch or a potato starch; a polysaccharide such as a crystalline cellulose (including a microcrystalline cellulose); a silicon dioxide or a silicate such as a light silicic anhydride or a synthetic aluminum silicate; a phosphate such as anhydrous dibasic calcium phosphate; and others.

The binder may include a water-soluble starch such as a pregelatinized starch or a partially pregelatinized starch; a polysaccharide such as agar, gum acacia (or gum arabic), dextrin, sodium alginate, a tragacanth gum, a xanthan gum, a hyaluronic acid, pectin, or a sodium chondroitin sulfate; a synthetic polymer such as a polyvinylpyrrolidone, a polyvinyl alcohol, a carboxyvinyl polymer, a polyacrylic acid-series polymer, a polylactic acid, or a polyethylene glycol; a cellulose ether such as a methyl cellulose, an ethyl cellulose, a carboxymethyl cellulose, a carboxymethyl cellulose sodium, a hydroxyethyl cellulose, a hydroxypropyl cellulose, or a hydroxypropyl methyl cellulose; and others.

The disintegrant may include calcium carbonate, a carboxymethyl cellulose or a salt thereof (e.g., a carmellose, a carmellose sodium, and a carmellose calcium, a croscarmellose sodium), a polyvinylpyrrolidone (e.g., a polyvinylpyrrolidone and a crosslinked polyvinylpyrrolidone (crosslinked povidone)), a low-substituted hydroxypropyl cellulose, a sodium starch glycolate, and others.

The lipid may include the above-exemplified wax, long-chain fatty acid ester, higher alcohol, phospholipid, higher fatty acid, metallic soap, and others.

300 parts by weight, and more preferably about 10 to 250 parts by weight (e.g., about 25 to 200 parts by weight) relative to 100 parts by weight of the active ingredient.

The lubricant may include, for example, a talc, magnesium stearate, calcium stearate, and a polyethylene glycol 6000.

Moreover, the additive may include a disintegrant aid, an antioxidation agent or an antioxidant, a surfactant, an emulsifier, a dispersing agent, a suspending agent, a dissolution aid, a thickener (e.g., a water-soluble polymer such as a carboxyvinyl polymer, a polyvinyl alcohol, or a gelatin; and a cellulose ether such as a carboxymethyl cellulose), a pH adjusting agent or a buffer (e.g., a citric acid-sodium citrate buffer), an antiseptic agent or a preservative (e.g., a paraben such as methyl paraben or butyl paraben), a fungicide or an antibacterial agent (e.g., a benzoic acid compound such as sodium benzoate), an antistatic agent, a corrigent or a masking agent (e.g., a sweetening agent), a coloring agent (a dye and a pigment such as colcothar), a deodorant or a perfume (e.g., an aromatic substance), an algefacient, an antifoaming agent, and others. These additives may also be used singly or in combination.

The solid preparation may be coated with a coating agent. The coating agent may include, for example, a saccharide or a sugar, a cellulose derivative such as an ethyl cellulose or a hydroxyethyl cellulose, a polyoxyethylene glycol, an enteric component (e.g., a cellulose acetate phthalate, a hydroxypropyl methyl cellulose phthalate, and a methyl methacrylate-(meth)acrylic acid copolymer, and eudragit (a methacrylic acid-acrylic acid copolymer)), and a gastric soluble component (e.g., a polymer containing a basic component such as a dialkylaminoalkyl (meth)acrylate (e.g., eudragit)).

Representative formulations (unit: mg) for a unit dosage form of a pharmaceutical composition (e.g., a solid preparation such as tablets) containing at least the fibrate compound (particularly, fenofibrate or a free acid or active metabolite thereof) as an active ingredient are as follows. Incidentally, since the porous carrier also serves as an excipient and the water-soluble polymer can serve as a binder, an additional excipient and/or binder is not essentially needed.

TABLE 1

Table 1

| | Range | Preferable range | More preferable range | Particularly preferable range |
|---|---|---|---|---|
| Total amount of active ingredients | 20 to 100 | 30 to 80 | 35 to 70 | 40 to 60 |
| Fibrate/Other active ingredients (weight ratio) | 60/40 to 100/0 | 70/30 to 100/0 | 75/25 to 100/0 | 80/20 to 100/0 |
| Active ingredient/Porous carrier (weight ratio) | 0.01/1 to 5/1 | 0.2/1 to 4/1 | 0.3/1 to 2.5/1 | 0.5/1 to 2/1 |
| Total amount of porous carriers | 20 to 100 | 30 to 80 | 40 to 70 | 45 to 60 |
| First porous carrier/Second porous carrier (weight ratio) | 50/50 to 100/0 | 60/40 to 100/0 | 70/30 to 100/0 | 75/25 to 100/0 |
| Additive component/Active ingredient (weight ratio) | 0.01/1 to 1/1 | 0.03/1 to 0.5/1 | 0.05/1 to 0.3/1 | 0.05/1 to 0.2/1 |
| Water-soluble polymer | 0 to 30 | 3 to 25 | 5 to 20 | 7 to 15 |
| Surfactant | 0 to 30 | 0.5 to 25 | 1 to 20 | 1.5 to 15 |
| Disintegrant | 10 to 100 | 20 to 80 | 30 to 70 | 40 to 60 |
| Excipient | 0 to 100 | 0 to 70 | 0 to 50 | 0 to 30 |
| Binder | 0 to 50 | 0 to 40 | 0 to 30 | 0 to 20 |
| Lubricant | 0 to 5 | 0.3 to 4 | 0.5 to 3.5 | 1 to 3 |

The carriers (or additives) may be used singly or in combination. The proportion of the carrier (or additive) is not particularly limited to a specific amount and may be, for example, about 1 to 500 parts by weight, preferably about 5 to The pharmaceutical composition of the present invention may be prepared by using a solid dispersion containing an active ingredient, and an carrier or additive component (a pharmaceutically acceptable component for a preparation), and if necessary another additive and the like with a conventional manner (for example, a production process described in Japanese Pharmacopoeia 15$^{th}$ edition or another process in accordance with the production process). The solid preparation may be, for example, produced by using a carrier or additive component (e.g., at least one carrier or additive selected from the group consisting of a binder, an excipient, and a disintegrant) together with an active ingredient-containing solid dispersion. For example, the granules may be prepared by granulating the active ingredient-containing solid dispersion and the carrier or additive component (a pharmaceutically acceptable component for a preparation) through extrusion granulation, spray granulation, or other means, and if necessary sizing or sieving resulting granule. The tablets may be produced by mixing the granulated product and the carrier or additive component and/or the additive if necessary, and compression-molding the resultant mixture. Moreover, if necessary, the compression-molded preparation may be coated. The capsules may be prepared by filling granules in a capsule.

Incidentally, as describe above, the solid dispersion of the present invention has an excellent compression moldability. Therefore, the solid dispersion is suitable for producing a pharmaceutical composition by a step for at least compressing the solid dispersion. For example, granules can be obtained by subjecting the solid dispersion, and if necessary, the additive component (e.g., an excipient) to a compression molding, crushing and sizing the resulting molded product. Tablets can be produced by subjecting a mixture of the solid dispersion and the additive component to a compression molding (a tablet compression). Tablets can be produced by subjecting a mixture of the granules and the additive component to a compression molding (a tablet compression).

The pharmaceutical composition of the present invention can be used for non-human animals and usually is applied for human beings. The content of the active ingredient in the preparation, the amount to be administered (or dose) of the preparation, and the administration schedule may be suitably selected in accordance with the species of the active ingredient, the subject to be administered, the age, body weight, sex, and condition (e.g., a performance status and a condition of a disease) of the subject, the duration (or period or schedule) of administration, the dosage form, the method (or route) of administration, and others. The content of the active ingredient in the preparation may be, for example, about 0.01 to 90% by weight, preferably about 0.05 to 80% by weight, and more preferably about 0.1 to 70% by weight (e.g., about 0.5 to 50% by weight) in terms of a solid content relative to the total amount of the preparation. More specifically, the content of the fibrate compound in the preparation may be, for example, about 1 to 90% by weight, preferably about to 80% by weight, and more preferably about 10 to 70% by weight (e.g., about 15 to 50% by weight). Moreover, the dose of the fibrate compound may be, for example, about 1 to 500 mg, preferably about 5 to 300 mg (e.g., about 10 to 250 mg), and more preferably about 30 to 200 mg (e.g., 50 to 150 mg) to an adult human being (body weight: about 60 kg) per day. The dose of the statin-series compound may be about 0.1 to 50 mg, preferably about 0.5 to 40 mg, and more preferably about 1 to 30 mg (e.g., about 1 to 10 mg) to an adult human being per day. The pharmaceutical composition of the present invention may be administered once a day, or twice or more times (e.g., about twice to fifth times) per day.

EXAMPLES

Hereinafter, the following examples are intended to describe this invention in further detail and should by no means be interpreted as defining the scope of the invention.

Examples 1 to 7

Preparations of Solid Dispersion and Tablet

Fenofibrate (5 g), sodium lauryl sulfate (SLS, 0.5 g), and hydroxypropyl methyl cellulose 2910 (HPMC 2910, 0.5 g) were dissolved in an ethanol/acetone mixture (volume ratio of 1:1) to prepare 50 ml of a solution (having a solution form at temperatures of 10° C. and 0° C.).

A spherical hydrated silicon dioxide (manufactured by Fuji Silysia Chemical Ltd., "SYLOSPHERE C-1510") as the first porous carrier and an amorphous light anhydrous silic acid (manufactured by Fuji Silysia Chemical Ltd., "SYLYSIA350") as a porous silicon-containing carrier were added to the resulting solution in a proportion shown in the following Table 2, and the resulting mixture was stirred.

TABLE 2

|  | Examples | | | | | | |
| --- | --- | --- | --- | --- | --- | --- | --- |
|  | 1 | 2 | 3 | 4 | 5 | 6 | 7 |
| First porous carrier | 5 g | 6 g | 7.5 g | 5 g | 5 g | 5 g | 3 g |
| Second porous carrier | — | — | — | 0.5 g | 1 g | 1.5 g | 1.5 g |

Incidentally, properties of the first spherical porous carrier and the second amorphous porous carrier are shown below.

First Porous Carrier

SYLOSPHERE C-1510

Heating weight loss (950° C., 2 hours): not more than 2.5% by weight
Infrared Absorption Spectrum:
The intensity ratios were as follows, where $I_0$ is an absorption intensity at a wave number of 3800 cm$^{-1}$, $I_1$ is that of 3650 cm$^{-1}$, $I_2$ is that of 3600 cm$^{-1}$, $I_3$ is that of 3550 cm$^{-1}$, $I_4$ is that of 3500 cm$^{-1}$, $I_5$ is that of 3450 cm$^{-1}$, $I_6$ is that of 3400 cm$^{-1}$, $I_7$ is that of 3350 cm$^{-1}$, $I_8$ is that of 3300 cm$^{-1}$, $I_9$ is that of 3200 cm$^{-1}$, and $I_{10}$ is that of 3100 cm$^{-1}$.

(1) $I_1/I_0=5.7$, $I_2/I_0=13.2$, $I_3/I_0=27.5$, $I_4/I_0=47.0$, $I_5/I_0=61.3$, $I_6/I_0=49.8$, $I_7/I_0=28.2$, $I_8/I_0=16.0$, $I_9/I_0=6.3$, $I_{10}/I_0=1.9$
(in some cases, $I_2/I_0=3.7$, $I_4/I_0=7.2$, $I_6/I_0=7.5$, $I_8/I_0=4.3$, $I_9/I_0=2.8$, $I_{10}/I_0=1.6$)
(2) $I_3/I_1=4.8$, $I_4/I_1=8.3$, $I_5/I_1=10.8$, $I_6/I_1=8.7$, $I_7/I_1=4.9$, $I_8/I_1=2.8$ Mean particle size: about 10 μm, mean pore size: 17 nm, pore volume (unit: ml/g): 1.5, specific surface area (unit: m$^2$/g): 520, and oil absorption (unit: ml/100 g): 250

FIG. 1 represents an infrared absorption spectrum of the first porous carrier "SYLOSPHERE C-1510".

Second Amorphous Porous Carrier

SYLYSIA 350

Heating weight loss (950° C., 2 hours): 5% by weight
Infrared Absorption Spectrum:
(1) $I_1/I_0=7.8$, $I_2/I_0=20.9$, $I_3/I_0=46.4$, $I_4/I_0=86.8$, $I_5/I_0=124.8$, $I_6/I_0=102.3$, $I_7/I_0=55.9$, $I_8/I_0=33.4$, $I_9/I_0=14.5$, $I_{10}/I_0=5.3$
(in some cases, $I_2/I_0=8.5$, $I_4/I_0=21.3$, $I_6/I_0=28.0$, $I_8/I_0=15.4$, $I_9/I_0=8.9$, $I_{10}/I_0=4.2$)
(2) $I_3/I_1=6.0$, $I_4/I_1=11.2$, $I_5/I_1=15.7$, $I_6/I_1=13.2$, $I_7/I_1=7.2$, $I_8/I_1=4.3$ Mean particle size: about 3.9 μm, mean pore size: 21 nm, pore volume (unit: ml/g): 1.7, specific surface area (unit: m$^2$/g): 300, and oil absorption (unit: ml/100 g): 310

Figure 2:
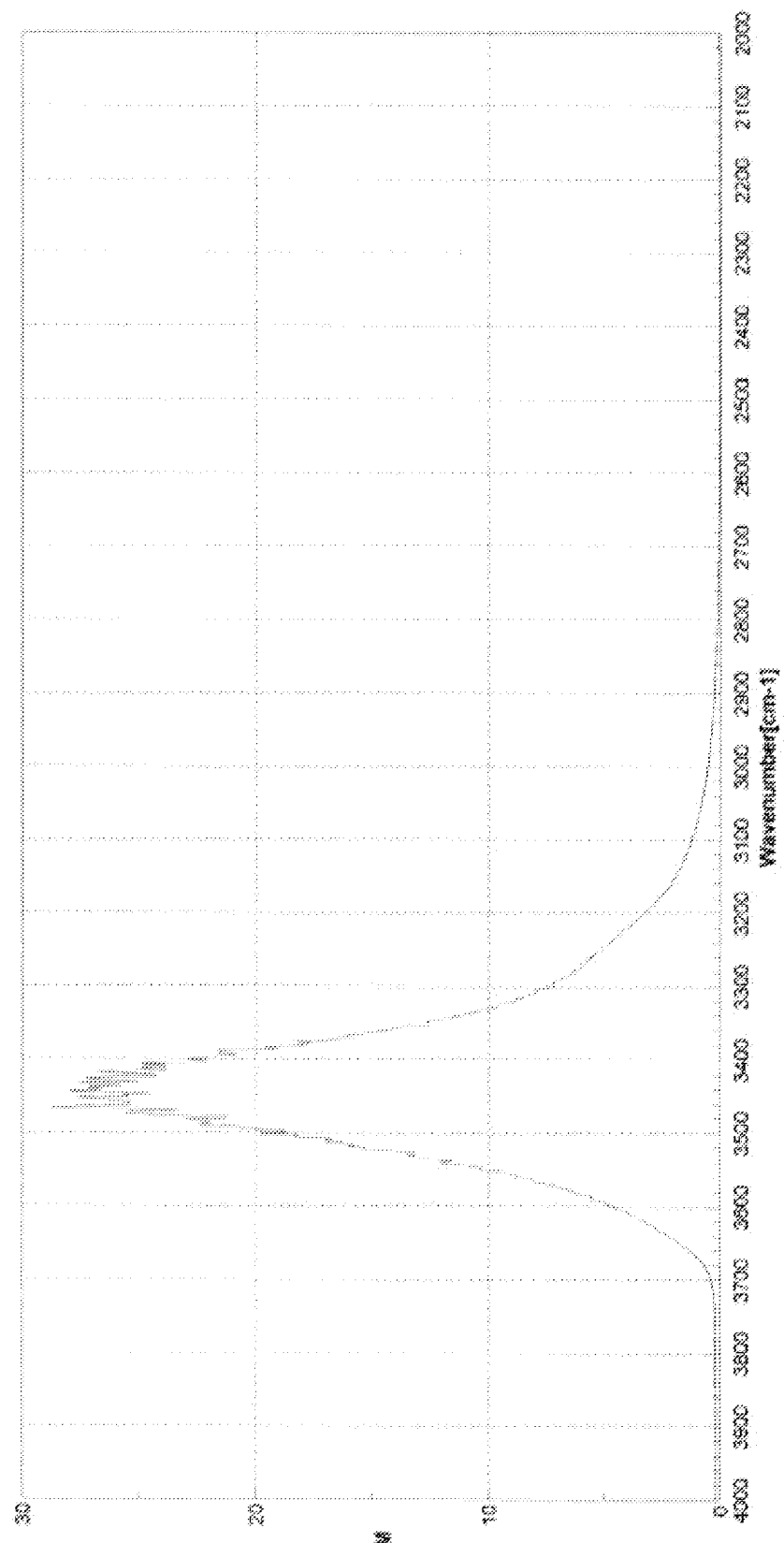
FIG. 2 represents an infrared absorption spectrum of the second porous carrier used in Examples 4 to 7.

FIG. 2 represents an infrared absorption spectrum of the second amorphous porous carrier "SYLYSIA 350".

The resulting suspension was spray dried by using a spray drier ("GS31" manufactured by Yamato Scientific Co., Ltd.) at 80° C. in a nitrogen atmosphere to give a solid dispersion powder. The resulting solid dispersion powder and a disintegrant (croscarmellose sodium) were weighed and mixed in a mortar, and then compressed at 50 kN to give a slug tablet. The slug tablet was crushed and passed through a sieve having an opening of 710 μm to give a granule. A lubricant (magnesium stearate) was added and mixed to the resulting granule, and the mixture was compressed at 5 kN to mold a tablet. The content of the fenofibrate in the tablet was measured by using a high-performance liquid chromatography (HPLC) and determined as about 48 mg per tablet. The formulation of the preparation (proportion of each component: parts by weight) are shown in Table 3.

TABLE 3

|  | Examples | | | | | | |
| --- | --- | --- | --- | --- | --- | --- | --- |
|  | 1 | 2 | 3 | 4 | 5 | 6 | 7 |
| Fenofibrate | 48 | 48 | 48 | 48 | 48 | 48 | 48 |
| First porous carrier | 48 | 57.6 | 72 | 48 | 48 | 48 | 28.8 |
| Second porous carrier | 0 | 0 | 0 | 4.8 | 9.6 | 14.4 | 14.4 |
| SLS | 4.8 | 4.8 | 4.8 | 4.8 | 4.8 | 4.8 | 4.8 |
| HPMC2910 | 4.8 | 4.8 | 4.8 | 4.8 | 4.8 | 4.8 | 4.8 |
| disintegrant | 48 | 48 | 48 | 48 | 48 | 48 | 48 |
| Lubricant | 2 | 2 | 2 | 2 | 2 | 2 | 2 |
| Total | 155.6 | 165.2 | 179.6 | 160.4 | 165.2 | 170.0 | 150.8 |

Control Preparation

A fenofibrate-pulverized preparation (LIPIDIL (registered trademark) Capsule 67 manufactured by ASKA Pharmaceutical Co., Ltd.), which has been obtained by co-pulverizing fenofibrate and a surfactant and contained 67 mg of fenofibrate, was used as a control preparation.

Dissolution Test

Figure 3:
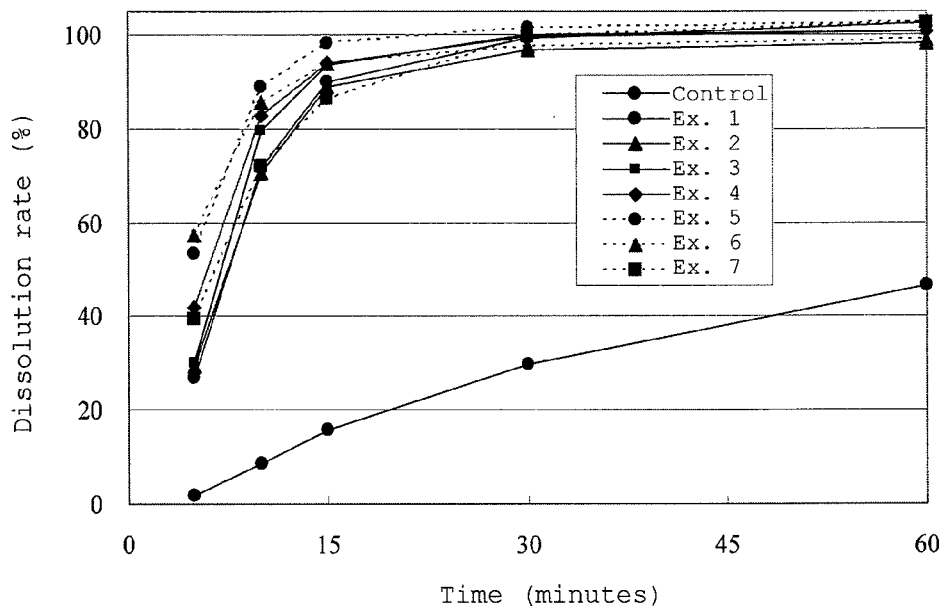
FIG. 3 represents a graph illustrating the results of the dissolution tests obtained from the tablets of Examples 1 to 7 and the control preparation.

For Examples 1 to 7 and the control preparation, a dissolution test (n=1 to 3) was performed under the following conditions by a paddle method, and the results shown in FIG. 3 were obtained.
Eluant: water (containing 1.0% by weight of polysorbate 80)
Number of revolutions: 50 revolutions per minute As apparent from FIG. 3, each tablet of Examples 1 to 7 had a higher solubility despite of a lower content of the active ingredient compared with the control preparation.

Absorbability

Dogs (male beagle, 21- to 24-month-old) were fasted overnight and fed for 30 minutes. After about 15 minutes, the tablet of Example 3 and 30 ml of water were orally administered to a first group, and the control preparation and 30 ml of water were orally administered to a second group. After the administration, each dog was freely allowed to have water. Before the administration, after the administration, and 0.5 to 25 hours (0.5 hour, 1 hour, 1.5 hours, 2 hours, 2.5 hours, 3 hours, 4 hours, 6 hours, 8 hours, and 24 hours) after the administration, the blood (about 1 mL) was collected from the right and left forearmcephalic vein of each dog. The blood was subjected to an extracting operation and then analyzed by using an LC/MS/MS (apparatus type: LC part: HP1100 manufactured by Agilent Technologies, MS part: Quattroll manufactured by Micromass) to calculate concentrations (μg/mL) of fenofibric acid (FA) and the reduced fenofibric acid (RFA) in the blood plasma and graph the relationship between the elapsed time and the total amount of fenofibric acid (FA) and the reduced fenofibric acid (RFA). The results are shown in FIG. 4.

Figure 4:
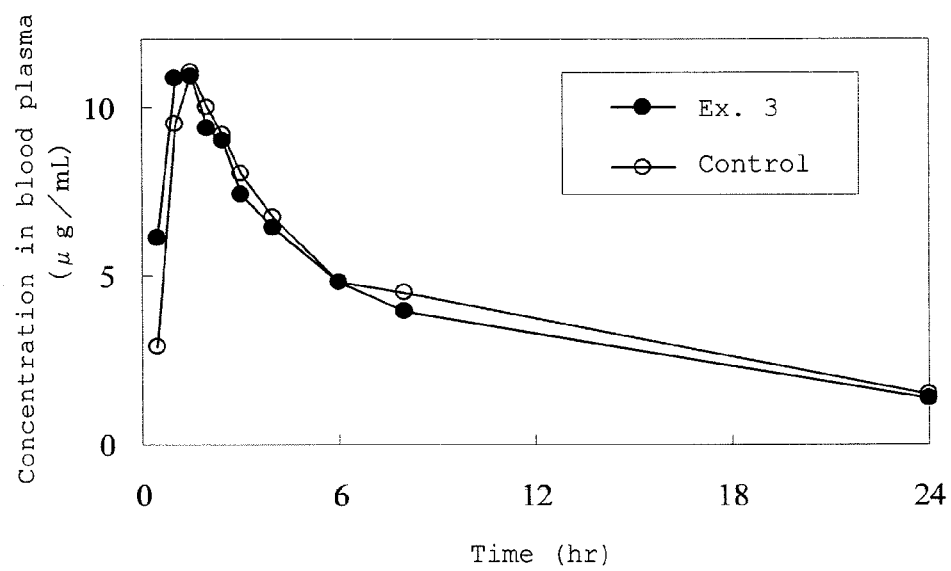
FIG. 4 represents a graph illustrating the results of the absorbability tests obtained from the tablet of Example 3 and the control preparation.

As apparent from FIG. 4, despite of a lower content of the active ingredient, the tablet of Example 3 had the absorbability equivalent to the control preparation.

Example 8

Preparations of Solid Dispersion and Tablet

A solid dispersion powder was obtained in the same manner as in Example 1 except that a spherical hydrated silicon dioxide having the following characteristics (manufactured by Fuji Silysia Chemical Ltd., "SYLOSPHERE C-1504") as the first porous carrier and HPC were used instead of the first spherical porous carrier (manufactured by Fuji Silysia Chemical Ltd., "SYLOSPHERE 0-1510") and HPMC 2910 in Example 1, respectively.

First Porous Carrier

SYLOSPHERE C-1504

Heating weight loss (950° C., 2 hours): not more than 2.5% by weight
Infrared Absorption Spectrum:
(1) $I_1/I_0=6.1$, $I_2/I_0=16.4$, $I_3/I_0=34.1$, $I_4/I_0=59.8$, $I_5/I_0=85.8$, $I_6/I_0=66.8$, $I_7/I_0=37.2$, $I_8/I_0=19.9$, $I_9/I_0=8.4$, $I_{10}/I_0=3.3$
(2) $I_3/I_1=5.6$, $I_4/I_1=9.8$, $I_5/I_1=14.0$, $I_6/I_1=10.9$, $I_7/I_1=6.1$, $I_8/I_1=3.3$
Mean particle size; about 4.5 μm, mean pore size: 17 nm, pore volume (unit: ml/g): 1.5, specific surface area (unit: $m^2/g$): 520, and oil absorption (unit: ml/100 g): 290

Figure 5:
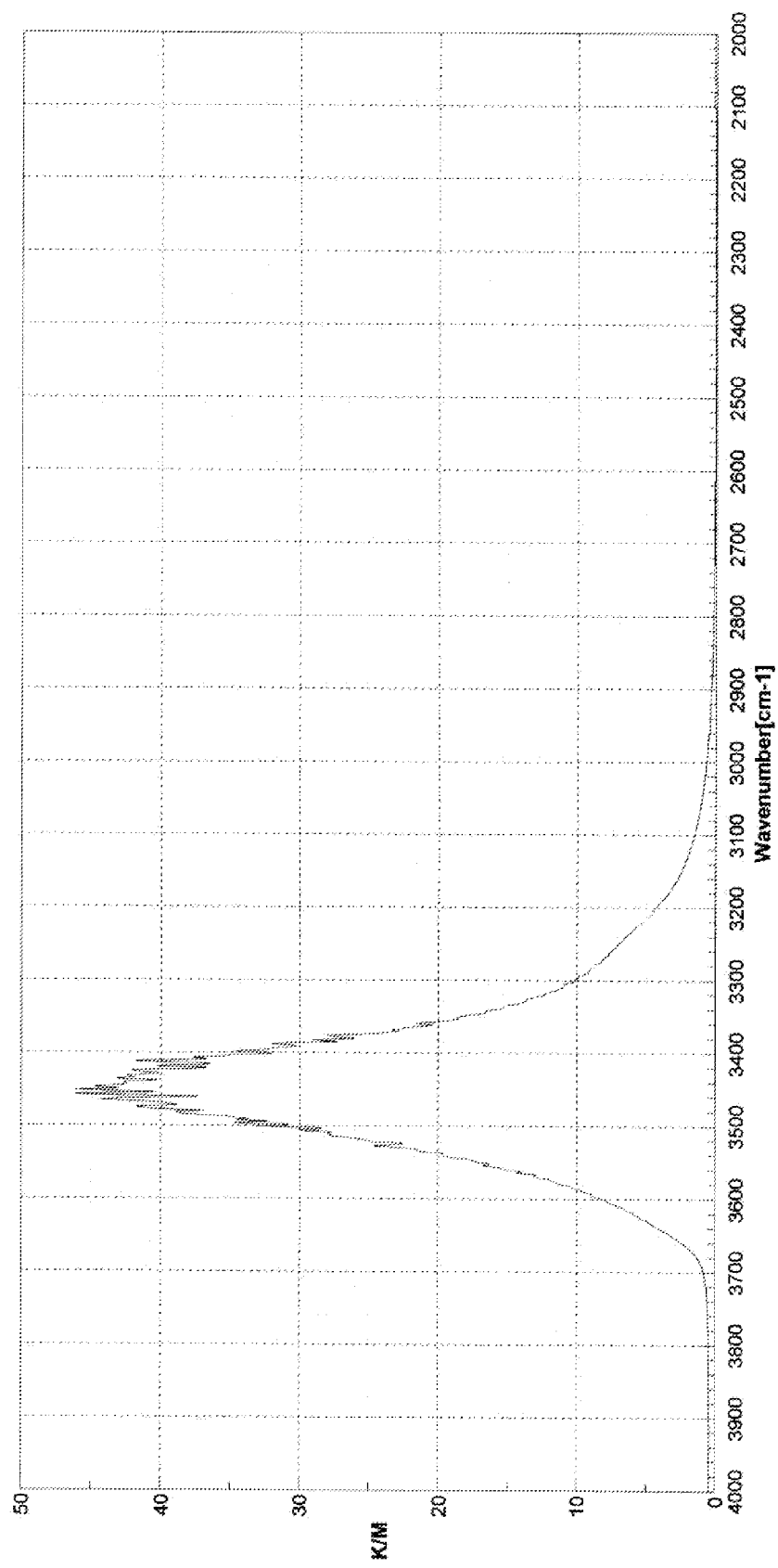
FIG. 5 represents an infrared absorption spectrum of the first porous carrier used in Example 8.

FIG. 5 represents an infrared absorption spectrum of the first spherical porous carrier "SYLOSPHERE C-1504".

The resulting solid dispersion powder, a disintegrant (croscarmellose sodium), and a lubricant (magnesium stearate) were used to give a tablet in the same manner as in Example 1. The formulation of the preparation per tablet (175.2 mg) was as follows: fenofibrate 53.3 mg, the first porous carrier 53.3 mg, SLS 1.9 mg, HPC 10.7 mg, disintegrant 53.5 mg, and lubricant 2.7 mg.

Dissolution Test

Figure 6:
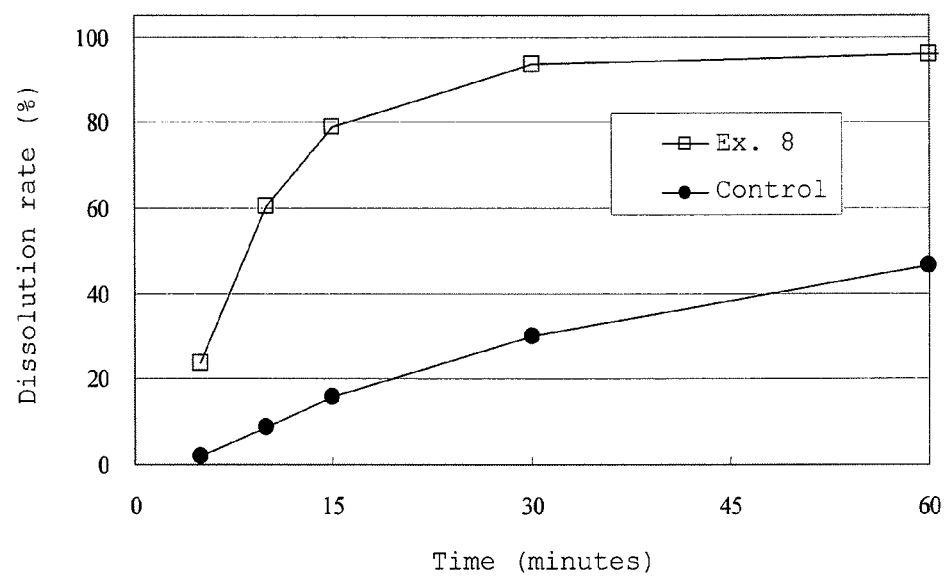
FIG. 6 represents a graph illustrating the results of the dissolution tests of the tablet obtained from Example 8 and the control preparation.

For the preparation of Example 8 and the control preparation, a dissolution test was performed by a paddle method in the same manner as in Example 1, and the results shown in FIG. 6 were obtained. As apparent from FIG. 6, the tablet of Example 8 had a higher solubility despite of a lower content of the active ingredient compared with the control preparation.

Example 9

Preparations of Solid Dispersion and Tablet

A solid dispersion powder was obtained in the same manner as in Example 1 except that a spherical hydrated silicon dioxide (manufactured by Fuji Silysia Chemical Ltd., "SYLOSPHERE C-1504") as the first porous carrier and HPC were used instead of the first spherical porous carrier and HPMC 2910 in Example 1, respectively, and that the proportion of fenofibrate and the first porous carrier was varied.

The resulting solid dispersion powder, a disintegrant (croscarmellose sodium), and a lubricant (magnesium stearate) were used to give a tablet in the same manner as in Example 1. The formulation of the preparation per tablet (172.7 mg) was as follows: fenofibrate 53.3 mg, the first porous carrier 48 mg, SLS 1.9 mg, HPC 10.7 mg, disintegrant 53.5 mg, and lubricant 5.3 mg.

Example 10

Preparations of Solid Dispersion and Tablet

A solid dispersion powder was obtained in the same manner as in Example 1 except that a spherical hydrated silicon dioxide (manufactured by Fuji Silysia Chemical Ltd., "SYLOSPHERE C-1504") as the first porous carrier and HPC were used instead of the first spherical porous carrier and HPMC 2910 in Example 1, respectively, and that the proportion of fenofibrate and the first porous carrier was varied.

The resulting solid dispersion powder, a disintegrant (croscarmellose sodium), and a lubricant (magnesium stearate) were used to give a tablet in the same manner as in Example 1. The formulation of the preparation per tablet (161.7 mg) was as follows: fenofibrate 53.3 mg, the first porous carrier 37 mg, SLS 1.9 mg, HPC 10.7 mg, disintegrant 53.5 mg, and lubricant 5.3 mg.

Example 11

The solid dispersion powder obtained from Example 8, a powdery pitavastatin (pitavastatin calcium), and a disintegrant (croscarmellose sodium) were weighed and mixed in a mortar, and then compressed at 50 kN to give a slug tablet. The slug tablet was crushed and passed through a sieve having an opening of 710 µm to give a granule. A lubricant (magnesium stearate) was added and mixed to the resulting granule, and the mixture was compressed at 50 kN to mold a tablet. The formulation of the preparation per tablet (175.2 mg) was as follows: fenofibrate 53.3 mg, pitavastatin 2 mg, the first porous carrier 53.3 mg, SLS 1.9 mg, HPC 10.7 mg, disintegrant 53.5 mg, and lubricant 2.7 mg.

Comparative Example 1

A fenofibrate-pulverized preparation contained 100 parts by weight of a pulverized fenofibrate having a mean particle size of 5 µm (which has been obtained by co-pulverizing fenofibrate and a surfactant (SLS)), an excipient (lactose hydrate), and a binder (pregelatinized starch). The fenofibrate-pulverized preparation and 3 parts by weight of a powdery pitavastatin (pitavastatin calcium) were mixed together. The resulting mixture, a disintegrant (crosslinked povidone), and a lubricant (magnesium stearate) were used to give a tablet in the same manner as in Example 1. The formulation of the tablet was as follows.

| | |
|---|---|
| Pulverized fenofibrate | 67.0 mg |
| Pitavastatin calcium | 2.0 mg |
| Lactose hydrate (excipient) | 33.6 mg |
| SLS (surfactant) | 2.3 mg |
| Pregelatinized starch (binder) | 10.1 mg |
| Crosslinked povidone (disintegrant) | 2.3 mg |
| Magnesium stearate (lubricant) | 1.7 mg |

Figure 7:
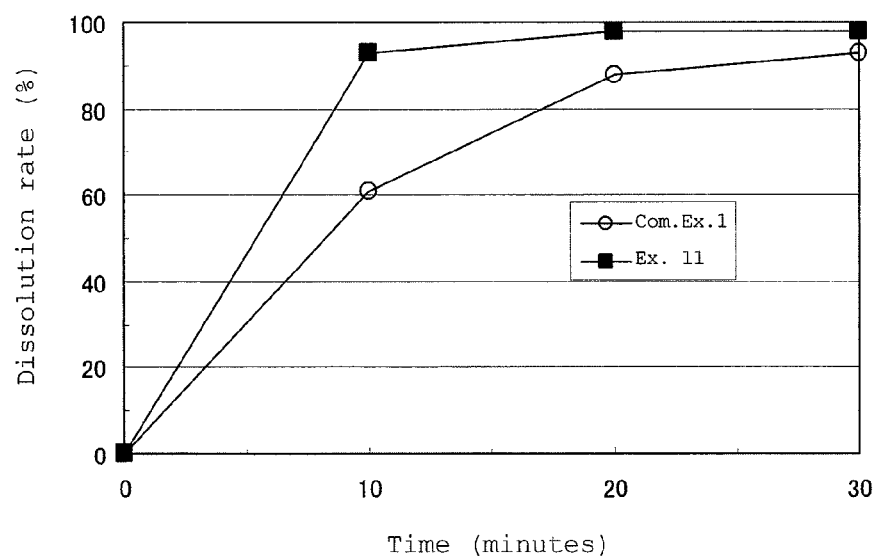
FIG. 7 represents a graph illustrating the results of the dissolution tests of the tablets obtained from Example 11 and Comparative Example 1.

The tablets of Example 11 and Comparative Example 1 were subjected to the above-mentioned dissolution test, and the results for fenofibrate shown in FIG. 7 were obtained. As apparent from FIG. 7, the preparation of Example 11 dissolves fenofibrate at a high dissolution rate. In contrast, the tablet of Comparative Example 1 has a low solubility of fenofibrate. Incidentally the dissolution of pitavastatin in the tablet of Example 11 and that in the tablet of Comparative Example 1 behave in the same manner. The dissolution rate was not less than 90% and not less than 95% at 10 minutes and 15 minutes, respectively. The dissolution test of pitavastatin was performed by using water as an eluant at the number of revolutions of 50 revolutions per minute in accordance with a paddle method (n=6). Moreover, the dissolution test of fenofibrate was performed by using sodium lauryl sulfate solution as an eluant at the number of revolutions of 100 revolutions per minute.

Example 12

The solid dispersion powder obtained from Example 8 and a powdery rosuvastatin (rosuvastatin calcium) were mixed in a proportion of fenofibrate/rosuvastatin=100/4.7 (weight ratio). The resulting mixture, a disintegrant (croscarmellose sodium), and a lubricant (magnesium stearate) were used to give a tablet in the same manner as in Example 1. The contents of the active ingredients in the tablet were measured by using a high-performance liquid chromatography (HPLC). The fenofibrate content was about 53.3 mg per tablet and the rosuvastatin content was 2.5 mg per tablet.

Example 13

The solid dispersion powder obtained from Example 8 and a powdery atorvastatin (atorvastatin calcium hydrate) were mixed in a proportion of fenofibrate/atorvastatin=100/9.4 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the atorvastatin content was 5 mg per tablet.

Example 14

The solid dispersion powder obtained from Example 8 and a powdery pravastatin were mixed in a proportion of fenofibrate/pravastatin=100/9.4 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the pravastatin content was 5 mg per tablet.

Example 15

The solid dispersion powder obtained from Example 8 and a powdery simvastatin were mixed in a proportion of fenofibrate/simvastatin=100/9.4 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the simvastatin content was 5 mg per tablet.

Example 16

The solid dispersion powder obtained from Example 8 and a powdery ezetimibe were mixed in a proportion of fenofibrate/ezetimibe=53.3/18.8 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the ezetimibe content was 10 mg per tablet.

Example 17

The solid dispersion powder obtained from Example 8 and a powdery candesartan cilexetil were mixed in a proportion of fenofibrate/candesartan cilexetil=100/3.8 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the candesartan cilexetil content was 2 mg per tablet.

Example 18

The solid dispersion powder obtained from Example 8 and a powdery losartan (losartan potassium) were mixed in a proportion of fenofibrate/losartan=100/47 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the losartan content was 25 mg per tablet.

Example 19

The solid dispersion powder obtained from Example 8 and a powdery telmisartan were mixed in a proportion of fenofibrate/telmisartan=100/37.5 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the telmisartan content was 20 mg per tablet.

Example 20

The solid dispersion powder obtained from Example 8 and a powdery amlodipine (amlodipine besilate) were mixed in a proportion of fenofibrate/amlodipine=100/4.7 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the amlodipine content was 2.5 mg per tablet.

Example 21

The solid dispersion powder obtained from Example 8 and a powdery aspirin were mixed in a proportion of fenofibrate/aspirin=100/5.6 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the aspirin content was 3 mg per tablet.

Example 22

The solid dispersion powder obtained from Example 8 and a powdery glimepiride were mixed in a proportion of fenofibrate/glimepiride=100/1.9 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the glimepiride content was 1 mg per tablet.

Example 23

The solid dispersion powder obtained from Example 8 and a powdery voglibose were mixed in a proportion of fenofibrate/voglibose=100/0.4 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the voglibose content was 0.2 mg per tablet.

Example 24

The solid dispersion powder obtained from Example 8 and a powdery pioglitazone (pioglitazone hydrochloride) were mixed in a proportion of fenofibrate/pioglitazone=100/28.1 (weight ratio). The resulting mixture, a disintegrant (croscarmellose sodium), and a lubricant (magnesium stearate) were used to give a tablet in the same manner as in Example 1. The contents of the active ingredients in the tablet were as follows: the fenofibrate content was about 53.3 mg per tablet and the pioglitazone content was 15 mg per tablet.

Example 25

Preparations of Solid Dispersion and Tablet

A solid dispersion powder was obtained in the same manner as in Example 1 except that a spherical hydrated silicon dioxide having the following characteristics (manufactured by Degussa, "AEROPERL 300/30") as the first porous carrier and HPC were used instead of the first spherical porous carrier (manufactured by Fuji Silysia Chemical Ltd., "SYLOSPHERE C-1510") and HPMC 2910 in Example 1, respectively.

First Porous Carrier

AEROPERL 300/30

Heating weight loss (950° C., 2 hours): not more than 2.0% by weight
Infrared Absorption Spectrum:
(1) $I_1/I_0$=4.1, $I_2/I_0$=9.5, $I_3/I_0$=17.7, $I_4/I_0$=29.1, $I_5/I_0$=37.1, $I_6/I_0$=31.3, $I_7/I_0$=19.1, $I_8/I_0$=12.3, $I_9/I_0$=6.1, $I_{10}/I_0$=2.7
(2) $I_3/I_1$=4.4, $I_4/I_1$=7.2, $I_5/I_1$=9.1, $I_6/I_1$=7.7, $I_7/I_1$=4.7, $I_8/I_1$=3.0

Mean particle size: about 30 µm, specific surface area (unit: m²/g): 300

Figure 8:
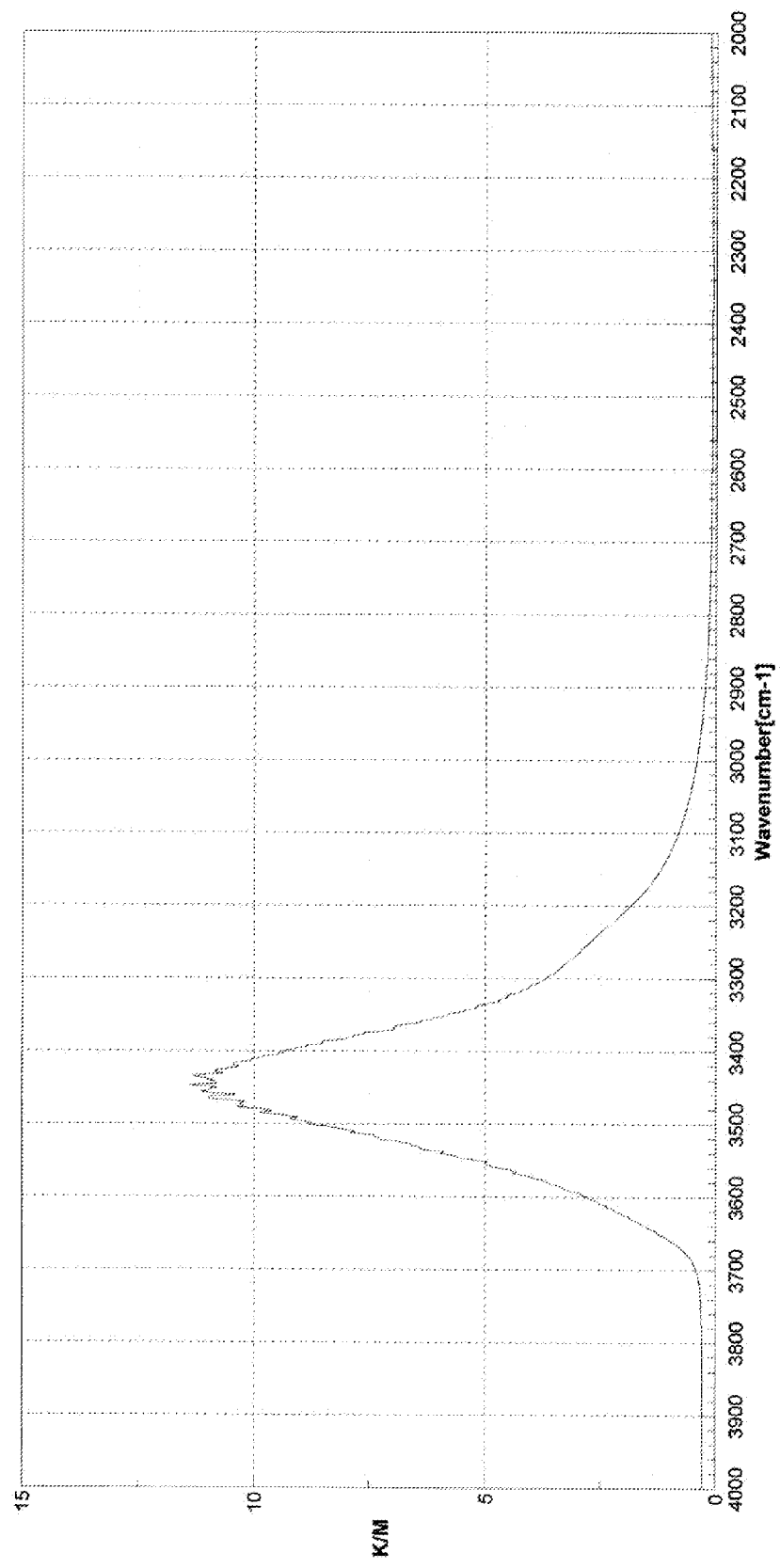
FIG. 8 represents an infrared absorption spectrum of the first porous carrier used in Example 25.

FIG. 8 represents an infrared absorption spectrum of the first spherical porous carrier "AEROPERL 300/30".

The resulting solid dispersion powder, a disintegrant (croscarmellose sodium and crosslinked povidone), and a lubricant (magnesium stearate) were used to give a tablet in the same manner as in Example 1. The formulation of the preparation per tablet (175.4 mg) was as follows: fenofibrate 53.3 mg, first porous carrier 53.3 mg, SLS 1.9 mg, HPMC 2910 5.35 mg, HPC 5.35 mg, disintegrant 53.5 mg (croscarmellose sodium 26.75 mg, crosslinked povidone 26.75 mg), and lubricant 2.7 mg.

Dissolution Test

Figure 9:
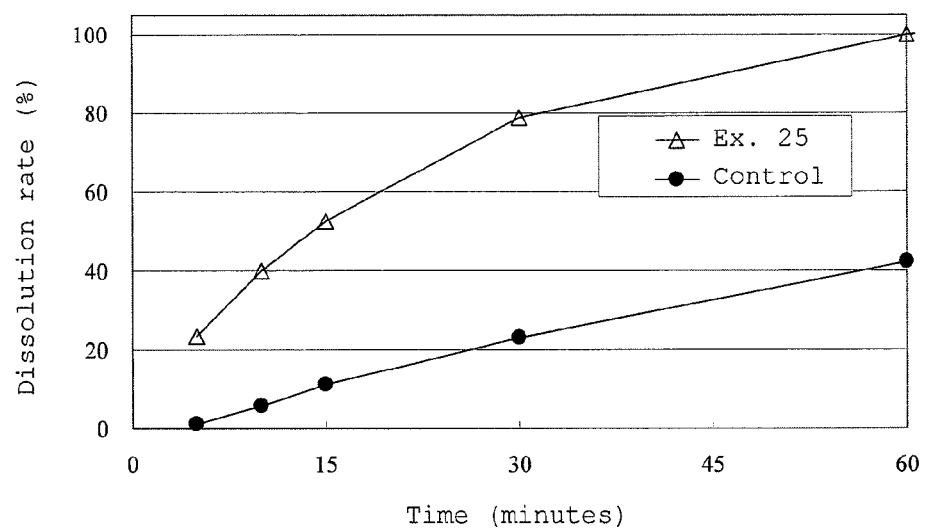
FIG. 9 represents a graph illustrating the results of the dissolution tests of the tablet obtained from Example 25 and the control preparation.

For the preparation of Example 25 and the control preparation, a dissolution test was performed by a paddle method in the same manner as in Example 1, and the results shown in FIG. 9 were obtained. As apparent from FIG. 9, the tablet of Example 25 had a higher solubility despite of a lower content of the active ingredient compared with the control preparation.

Preparation Example 1

Tablets

A solid dispersion was obtained by spray-drying in the same manner as Example 1. The resulting solid dispersion and the following additive components were mixed together, and then compressed at 5 kN to mold tablets. Incidentally, the following proportion shows a proportion (% by weight) in the tablet.

| Solid dispersion of Example 1 | 41% by weight |
|---|---|
| Lactose | 39% by weight |
| Crystalline cellulose | 9% by weight |
| Crosslinked povidone | 9% by weight |
| Talc | 1% by weight |
| Sucrose fatty acid ester | 1% by weight |

Preparation Example 2

Tablets

A solid dispersion was obtained by spray-drying in the same manner as Example 5. The resulting solid dispersion and the following additive components were mixed together, and then compressed at 5 kN to mold tablets. Incidentally, the following proportion shows a proportion (% by weight) in the tablet.

| Solid dispersion of Example 5 | 54% by weight |
|---|---|
| D-mannitol | 22% by weight |
| Crosslinked povidone | 22% by weight |
| Magnesium stearate | 2% by weight |

Preparation Example 3

Capsules

A solid dispersion powder was obtained by spray-drying in the same manner as Example 7. The resulting solid dispersion powder, D-mannitol, and croscarmellose sodium were mixed, and the mixture was compressed at 20 kN to mold slug tablets. The slug tablet was crushed and passed through a sieve having an opening of 710 µm to give a granule. A capsule was obtained by filling the resulting granule in a gelatin capsule in an amount of about 197 mg per capsule. Incidentally, the following was a proportion (% by weight) relative to 100% by weight of the contents of the capsule.

| Solid dispersion of Example 7 | 52% by weight |
|---|---|
| D-mannitol | 24% by weight |
| Croscarmellose sodium | 24% by weight |

INDUSTRIAL APPLICABILITY

The solid dispersion and pharmaceutical composition of the present invention have remarkably improved solubility (dissolution rate) or dispersibility and the bioavailability of the active ingredient, and can allow a reduced content of the active ingredient in the pharmaceutical preparation and realize a compact or small preparation (or dosage form). Therefore, the pharmaceutical composition has an excellent easiness of dosing and improves the patient compliance effectively. The solid dispersion and the pharmaceutical composition of the present invention is utilized for an agent for prophylactic (or preventing) and/or treating various diseases, for example, metabolic syndrome, hyperlipemia, diabetes, and diabetes complication, depending on the species of the active ingredient.

The invention claimed is:
1. A solid dispersion comprising:
an active ingredient having a solubility in water at 25° C. of not more than 1 mg/mL, and
a powdery porous carrier impregnated with and supporting the active ingredient,
wherein the powdery porous carrier comprises a first porous silicon-containing carrier having a heating loss of not more than 2.5% by weight at a temperature of 950° C. for 2 hours,
wherein the first porous silicon-containing carrier has a mean pore size of 15 to 20 nm, an oil absorption of 230 to 320 ml/100 g, a mean particle size of 3 to 15 µm, and a specific surface area of 400 to 600 m²/g, and
wherein the first porous silicon-containing carrier satisfies at least one of the following intensity ratios in an infrared absorption spectrum:
(1-2) intensity ratio ($I_2/I_0$): 11 to 17;
(1-3) intensity ratio ($I_3/I_0$): 20 to 40;
(1-4) intensity ratio ($I_4/I_0$): 35 to 73;
(1-5) intensity ratio ($I_5/I_0$): 40 to 110;
(1-6) intensity ratio ($I_6/I_0$): 35 to 85;
(1-7) intensity ratio ($I_7/I_0$): 23 to 47;
(1-8) intensity ratio ($I_8/I_0$): 14 to 27;
(2-2) intensity ratio ($I_4/I_1$): 7.7 to 10.5;
(2-3) intensity ratio ($I_5/I_1$): 9.5 to 15;
(2-4) intensity ratio ($I_6/I_1$): 8 to 12;
wherein $I_0$ is an absorption intensity at a wave number of 3800 cm$^{-1}$, $I_1$ is that of 3650 cm$^{-1}$, $I_2$ is that of 3600 cm$^{-1}$, $I_3$ is that of 3550 cm$^{-1}$, $I_4$ is that of 3500 cm$^{-1}$, $I_5$ is that of 3450 cm$^{-1}$, $I_6$ is that of 3400 cm$^{-1}$, $I_7$ is that of 3350 cm$^{-1}$, $I_8$ is that of 3300 cm$^{-1}$, $I_9$ is that of 3200 cm$^{-1}$, and $I_{10}$ is that of 3100 cm$^{-1}$, and wherein the powdery porous carrier further comprises a second porous silicon-containing carrier having a heating loss of not less than 4.5% by weight at a temperature of 950° C. for 2 hours.

2. The solid dispersion according to claim 1, wherein the first porous silicon-containing carrier is spherical.

3. The solid dispersion according to claim 1, wherein the first porous silicon-containing carrier satisfies at least one of the following intensity ratios in an infrared absorption spectrum:
- (1-2) intensity ratio ($I_2/I_0$): 13.2 to 16.4;
- (1-3) intensity ratio ($I_3/I_0$): 27.5 to 34.1;
- (1-4) intensity ratio ($I_4/I_0$): 47.0 to 59.8;
- (1-5) intensity ratio ($I_5/I_0$): 61.3 to 85.8;
- (1-6) intensity ratio ($I_6/I_0$): 49.8 to 66.8;
- (1-7) intensity ratio ($I_7/I_0$): 28.2 to 37.2;
- (1-8) intensity ratio ($I_8/I_0$): 16.0 to 19.9;
- (2-2) intensity ratio ($I_4/I_1$): 8.3 to 9.8;
- (2-3) intensity ratio ($I_5/I_1$): 10.8 to 14.0;
- (2-4) intensity ratio ($I_6/I_1$): 8.7 to 10.9;

wherein $I_0$, $I_1$, $I_2$, $I_3$, $I_4$, $I_5$, $I_6$, $I_7$ and $I_8$ are as defined in claim 1.

4. The solid dispersion according to claim 1, wherein the first porous silicon-containing carrier is a spherical silica having a heating loss of not more than 2% by weight at a temperature of 950° C. for 2 hours.

5. The solid dispersion according to claim 1, wherein the first porous silicon-containing carrier is a spherical silica, comprises a monodisperse particle, has a number of pores having a nanometer size inside the particle, and in the carrier, a void space occupies 50 to 85% of the volume of the particle.

6. The solid dispersion according to claim 1, wherein the first porous silicon-containing carrier has an apparent specific gravity of 10 to 50 ml/5 g.

7. The solid dispersion according to claim 1, wherein the porous carrier comprises the first porous silicon-containing carrier having a heating loss of not more than 2.5% by weight at a temperature of 950° C. for 2 hours, and the second porous silicon-containing carrier, wherein the weight ratio of the first porous silicon-containing carrier relative to the second porous silicon-containing carrier is 50/50 to 100/0.

8. The solid dispersion according to claim 1, wherein the active ingredient is at least one agent selected from the group consisting of a hypolipidemic agent, a hypertension-treating agent, an antiobesity agent, a diuretic agent, an antithrombolic agent, a diabetic agent, and an agent for treating a diabetic complication.

9. The solid dispersion according to claim 1, wherein the active ingredient is a fibrate compound.

10. The solid dispersion according to claim 1, wherein the active ingredient is at least one compound selected from the group consisting of bezafibrate, clinofibrate, clofibrate, fenofibrate, beclobrate, binifibrate, ciprofibrate, etofibrate, gemfibrozil, nicofibrate, pirifibrate, ronifibrate, symfibrate, simfibrate, and theofibrate, or a free acid thereof, an active metabolite thereof, or a salt thereof.

11. The solid dispersion according to claim 1, wherein the active ingredient is supported on the powdery porous carrier in a proportion of 0.01 to 5 parts by weight relative to 1 part by weight of the powdery porous carrier.

12. The solid dispersion according to claim 1, wherein the active ingredient is a crystalline active ingredient and is supported in an amorphous form on the porous carrier.

13. The solid dispersion according to claim 1, which further comprises a water-soluble additive component, wherein the water-soluble additive component is supported on the porous carrier.

14. The solid dispersion according to claim 13, wherein the total amount of the additive component is 1 to 50 parts by weight relative to 100 parts by weight of the active ingredient.

15. The solid dispersion according to claim 13, wherein the active ingredient and the water-soluble additive component are uniformly supported throughout the porous carrier by impregnation.

16. A process for producing a solid dispersion, which comprises
impregnating a powdery porous carrier comprising the first and second porous silicon-containing carriers according to claim 1 with a solution comprising an organic solvent and an active ingredient having a low solubility in water to obtain a mixture, and
removing the organic solvent from the mixture to obtain a solid dispersion comprising the powdery porous carrier and the active ingredient supported on the powdery porous carrier.

17. The process according to claim 16, wherein the solution comprising the organic solvent and the active ingredient is in a liquid form at a temperature of 10° C., and the powdery porous carrier is impregnated with the solution by immersing the powdery porous carrier in the solution at room temperature, and the organic solvent is removed by drying the mixture.

18. The process according to claim 16, wherein the mixture of the powdery porous carrier and the solution containing the organic solvent and the active ingredient is spray-dried.

19. A pharmaceutical composition comprising the solid dispersion according to claim 1.

20. The pharmaceutical composition according to claim 19, which comprises a plurality of active ingredients containing at least one active ingredient having a solubility in water at 25° C. of not more than 1 mg/mL, wherein at least the active ingredient having the solubility in water at 25° C. of not more than 1 mg/mL is supported on the powdery porous carrier, and the powdery porous carrier comprises the first and second porous silicon-containing carriers.

21. The pharmaceutical composition according to claim 19, which comprises a first active ingredient having a first dosage and a second active ingredient having a second dosage lower than the first dosage, wherein the first active ingredient, and optionally the second active ingredient, has/have a solubility in water at 25° C. of not more than 1 mg/mL, wherein the first active ingredient and optionally the second active ingredient is/are supported on the powdery porous carrier, and the powdery porous carrier comprises the first and second porous silicon-containing carriers.

22. The pharmaceutical composition according to claim 19, which comprises a fibrate compound and a statin-series compound, wherein at least the fibrate compound is supported on the powdery porous carrier.

23. The pharmaceutical composition according to claim 19, further comprising at least one additive component selected from the group consisting of an excipient, a binder, a disintegrant, and a lubricant.

24. The pharmaceutical composition according to claim 19, which is a solid preparation formed from the solid dispersion by a compression molding.

25. A process for producing a pharmaceutical composition, which comprises at least a step of compressing the solid dispersion according to claim 1.

26. The solid dispersion according to claim 1, wherein the first porous silicon-containing carrier has:
a heating loss of not more than 2.5% by weight at a temperature of 950° C. for 2 hours,
an oil absorption of 250 ml/100 g or 290 ml/100 g,
a mean particle size of about 10 μm or about 4.5 μm, and
a specific surface area of 520 m$^2$/g.

* * * * *